United States Patent [19]
Edie et al.

[11] Patent Number: 5,137,879
[45] Date of Patent: Aug. 11, 1992

[54] FUROPYRIMIDIN-4-IMINE DERIVATIVES

[75] Inventors: Ronnie G. Edie, Greenfield; Ronald E. Hackler, Eriks V. Krumkalns, both of Indianapolis, all of Ind.

[73] Assignee: DowElanco, Indianapolis, Ind.

[21] Appl. No.: 502,364

[22] Filed: Mar. 30, 1990

[51] Int. Cl.$^5$ ............... A01N 43/54; C07D 491/048; C07F 7/10

[52] U.S. Cl. .................. 514/63; 514/232.8; 514/234.2; 514/258; 514/267; 544/115; 544/117; 544/229; 544/250; 544/278

[58] Field of Search ............... 544/115, 117, 229, 250, 544/278; 514/63, 232.8, 234.2, 258, 267

[56] References Cited

U.S. PATENT DOCUMENTS

| | | | |
|---|---|---|---|
| 3,632,763 | 1/1972 | Hess et al. | 424/251 |
| 4,007,187 | 2/1977 | Fauran et al. | 260/256.4 F |
| 4,119,584 | 4/1980 | Cox et al. | 424/251 |
| 4,725,599 | 2/1988 | Glazer et al. | 514/258 |
| 4,835,157 | 5/1989 | Press et al. | 514/258 |

OTHER PUBLICATIONS

A. Jorgensen et al., "Phosphorus Pentoxide in Organic Synthesis, Part XXII," *Chemica Scripta* 1985, 25, 227–229.

F. Johannsen et al., "Phosphorus Pentoxide in Organic Synthesis, Part XXVI," *Chemica Scripta* 1986, 26, 337–42.

*Chemica Abstracts*, 80:37150b (1974), abstracting Japan Kokai 73 81,893.

*Chemical Abstracts*, 80:48031q (1974), abstracting Japan Kokai 73 81,894.

*Chemical Abstracts*, 80:96012 (1974), abstracting Japan Kokai 73 78,199.

*Primary Examiner*—Mukund J. Shah
*Assistant Examiner*—Jyothsna Venkat
*Attorney, Agent, or Firm*—Donald R. Stuart

[57] ABSTRACT

Compounds of the formula

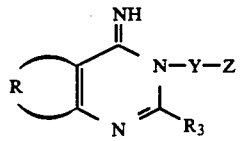

where

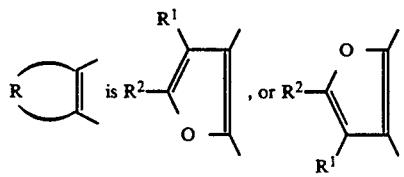

$R^1$ is H, $C_1$–$C_4$ alkyl, or phenyl optionally substituted with halo, ($C_1$–$C_4$) alkyl, ($C_1$–$C_4$) alkoxy, halo ($C_1$–$C_4$) alkyl, or halo ($C_1$–$C_4$) alkoxy;

$R^2$ is H, ($C_1$–$C_4$) alkyl, nitro, halo; or $R^1$ and $R^2$ combine to form —$(CH_2)_4$—;

$R^3$ is H, ($C_1$–$C_4$) alkyl, halo ($C_1$–$C_4$ alkyl, phenyl, or substituted phenyl;

Y is a bivalent hydrocarbon radical two to six carbon atoms long, optionally substituted with ($C_1$–$C_4$) alkyl, ($C_2$–$C_4$) alkenyl or -alkynyl, branched ($C_3$–$C_7$) alkyl, ($C_3$–$C_7$) cycloalkyl or cycloalkenyl, halo, halo ($C_1$–$C_4$) alkyl, halo ($C_1$–$C_4$) alkoxy, hydroxy, or ($C_1$–$C_4$) acyl; and Z is an optionally substituted cycloalkyl, cycloalkenyl, phenyl, naphtyl, or pyridyl group;

are useful as fungicides and as intermediates in making other pesticides.

20 Claims, No Drawings

FUROPYRIMIDIN-4-IMINE DERIVATIVES

FIELD OF THE INVENTION

This invention provides new compounds that have excellent plant fungicide activity. Some of the compounds have also demonstrated insecticidal and miticidal activity. The invention also provides compositions and combination products that contain a compound of the invention as active ingredient, as well as providing fungicidal, miticidal, and insecticidal methods.

There is an acute need for new fungicides, insecticides, and miticides, because target pathogens are rapidly developing resistance to currently used pesticides. Widespread failure of N-substituted azole fungicides to control barley mildew was observed in 1983, and has been attributed to the development of resistance. At least 50 species of fungi have developed resistance to the benzimidazole fungicides. The field performance of DMI (demethylation inhibitor) fungicides, which are now widely relied on to protect cereal crops from powdery mildew, has declined since they were introduced in the 1970's. Even recently introduced fungicides, like the acylalanines, which initially exhibited excellent control of potato late blight and grape downy mildew in the field, have become less effective because of widespread resistance. Similarly, mites and insects are developing resistance to the miticides and insecticides in current use. Resistance to insecticides in arthropods is widespread, with at least 400 species resistant to one or more insecticides. The development of resistance to some of the older insecticides, such as DDT, the carbamates, and the organophosphates, is well known. But resistance has even developed to some of the newer pyrethroid insecticides and miticides. Therefore a need exists for new fungicides, insecticides, and miticides.

SUMMARY OF THE INVENTION

This invention provides compounds of the formula (1):

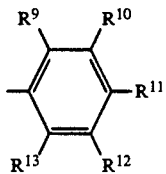

wherein

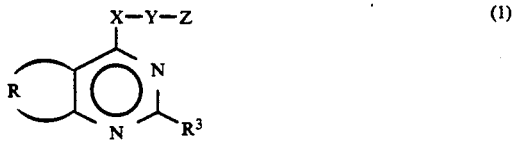

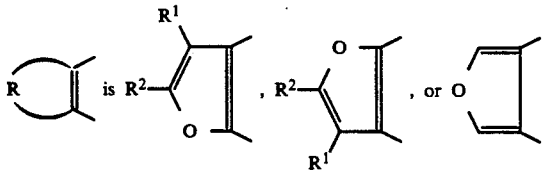

$R^1$ is H, $(C_1-C_4)$ alkyl, or phenyl optionally substituted with halo, $(C_1-C_4)$ alkyl, $(C_1-C_4)$ alkoxy, halo $(C_1-C_4)$ alkyl, or halo $(C_1-C_4)$ alkoxy;

$R^2$ is H, $C_1-C_4$ alkyl, nitro, halo; or $R^1$ and $R^2$ combine to form $-(CH_2)_4-$;

$R^3$ is H, $C_1-C_4$ alkyl, halo $(C_1-C_4)$ alkyl, phenyl, or substituted phenyl;

—XYE combine to form IH-1,2,4-triazol-1-yl; or

X is O, S, $NR^4$, or $CR^5R^6$, where $R^4$ is H, $(C_1-C_4)$ alkyl, or $(C_1-C_4)$ acyl, and $R^5$ and $R^6$ are independently H, $(C_1-C_4)$ alkyl, $(C_2-C_4)$ alkenyl or -alkynyl, CN, or OH, or $R^5$ and $R^6$ combine to form a carbocyclic ring containing four to six carbon atoms; and —YE combine to form a $C_5-C_{12}$ saturated or unsaturated hydrocarbon chain, straight chain or branched; optionally including a hetero atom selected from O, $NR^4$, S, SO, $SO_2$, or $SiR^7R^8$, where $R^4$ is as defined above and $R^7$ and $R^8$ are independently $(C_1-C_4)$ alkyl, $(C_3-C_4)$ branched alkyl, phenyl, or substituted phenyl, and optionally substituted with $(C_1-C_4)$ alkyl, $(C_2-C_4)$ alkenyl or -alkynyl, branched $(C_3-C_7)$ alkyl, $(C_3-C_7)$ cycloalkyl or -cycloalkenyl, halo, halo $(C_1-C_4)$ alkyl, halo $(C_1-C_4)$ alkoxy, hydroxy, or $(C_1-C_4)$ acyl; or Y is a bond or a bivalent hydrocarbon radical one to six carbon atoms long, optionally including a carbocyclic ring, and optionally including a hetero atom selected from O, $NR^4$, S, SO, $SO_2$, or $SiR^7R^8$, where $R^4$, $R^7$, and $R^8$ are as defined above, and optionally substituted with $(C_1-C_4)$ alkyl, $(C_2-C_4)$ alkenyl or -alkynyl, branched $(C_3-C_7)$ alkyl, $(C_3-C_7)$ cycloalkyl or -cycloalkenyl, halo, halo $(C_1-C_4)$ alkyl, halo $(C_1-C_4)$ alkoxy, hydroxy, or $(C_1-C_4)$ acyl; and Z is (a) $(C_3-C_8)$ cycloalkyl or cycloalkenyl, optionally substituted with $(C_1-C_4)$ alkyl, $(C_1-C_4)$ alkoxy, halo $(C_1-C_4)$ alkyl, halo $(C_1-C_4)$ alkoxy, halo, hydroxy, or $(C_1-C_4)$ acyl;

(b) a phenyl group of the formula (2)

$$\begin{array}{c} R^9 \quad R^{10} \\ \phantom{XX}\diagup\diagdown \\ \phantom{XXX}—R^{11} \\ \phantom{XX}\diagdown\diagup \\ R^{13} \quad R^{12} \end{array} \quad (2)$$

where
$R^9$ to $R^{13}$ are independently
H,
halo,
I,
$(C_3-C_8)$ cycloalkyl or -cycloalkenyl,
phenoxy, or
substituted phenoxy,
phenylthio, or substituted phenylthio,
phenyl, or substituted phenyl,
$NO_2$,
acetoxy,
OH,
CN,
SiR
$SiR^7R^{14}$ or $OSiR^7RsR^{14}$, where $R^7$, and $R^8$ are as defined above and $R^{14}$ is $(C_1-C_4)$ alkyl, $(C_3-C_4)$ branched alkyl, phenyl, or substituted phenyl,
$NR^{15}R^{16}$, where $R^{15}$ and $R^{16}$ are independently H, $(C_1-C_4)$ alkyl, or $(C_1-C_4)$ acyl,
$S(O)R^{17}$, or $SO_2R^{17}$, where $R^{17}$ is $(C_1-C_{100})$ alkyl, phenyl, or substituted phenyl;
a $C_1-C_{12}$ saturated or unsaturated hydrocarbon chain, straight chain or branched optionally including a hetero atom selected from O, S, SO, $SO_2$, $NR^4$ or $SiR^7R^8$, where $R^7$ and $R^8$ are as defined above, and optionally substituted with halo, halo $(C_1-C_4)$ alkoxy, hydroxy, $(C_3-C_8)$ cycloalkyl or cycloalkenyl, $(C_1-C_4)$ acyl, phenoxy, substituted phenoxy, phenyl, substituted phenyl, phenylthio, or substituted phenylthio;

($C_1$–$C_7$) alkoxy optionally substituted with halo, phenyl, substituted phenyl, ($C_3$–$C_8$) cycloalkyl or cycloalkenyl, phenoxy, or substituted phenoxy;

($C_1$–$C_7$) alkylthio optionally substituted with halo, phenyl, substituted phenyl, ($C_3$–$C_8$) cycloalkyl or cycloalkenyl, phenoxy or substituted phenoxy; or $R^{10}$ and $R^{11}$ combine to form —O—$CF_2$—O— or —O—$(CH_2)_2$—O—;

(c) a furyl group of formula (3)

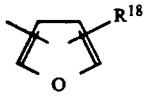

(3)

wherein $R^{18}$ is H, halo, halomethyl, CN, $NO_2$, ($C_1$–$C_4$) alkyl, ($C_3$–$C_4$) branched alkyl, phenyl, ($C_1$–$C_4$) alkoxy;

(d) a thienyl group of the formula (4)

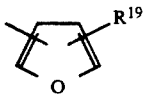

(4)

where $R^{19}$ is $R^{18}$ as defined in paragraph (c) or thienyl;

(e) a group of formula (5) or (6)

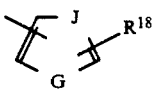

(5)

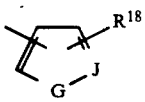

(6)

where $R^{18}$ is as defined in paragraph (c), J is N or CH, and G is O, $NR^{20}$, or S, provided that if J is not N then G is $NR^{20}$, where $R^{20}$ is H, ($C_1$–$C_4$) alkyl, ($C_1$–$C_4$) acyl, phenylsulfonyl, or substituted phenylsulfonyl;

(f) a group selected from optionally substituted naphthyl, dihydronaphthyl, tetrahydronaphthyl, and decahydronaphthyl;

optionally substituted pyridyl;

optionally substituted indolyl;

1,3-benzodioxolyl;

2,6-dimethyl-4-morpholinyl; and 1-adamantyl;

or an acid addition salt of a compound of formula (1); provided that:

if the compound of formula (1) is a furo[2,3-d]pyrimidin-4-amine, then Y is an alkylene chain two to six carbon atoms long, optionally including a carbocyclic ring, and optionally including a hetero atom selected from O, $NR^4$, S, SO, $SO_2$, or $SiR^7R^8$, where $R^4$, $R^7$, and $R^8$ are as defined above, and optionally substituted with ($C_1$–$C_4$) alkyl, ($C_2$–$C_4$) alkenyl or -alkenyl, branched ($C_3$–$C_7$) alkyl, ($C_3$–$C_7$) cycloalkyl or -cycloalkenyl, halo, hydroxy, or acetyl; and Z is one of the groups defined in paragraphs (a) through (f).

Compounds of formula (1) are useful as fungicides, insecticides, and miticides.

The invention also provides novel compounds of the formula (7)

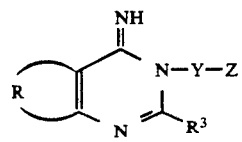

(7)

where R 

where $R^3$ are as defined in formula (1);

Y is an alkylene chain two to six carbon atoms long, optionally including a carbocyclic ring, and optionally including a hetero atom selected from O, $NR^4$, S, SO, $SO_2$, or $SiR^7R^8$, where $R^4$, $R^7$, and $R^8$ are as defined above, and optionally substituted with ($C_1$–$C_4$) alkyl, ($C_2$–$C_4$) alkenyl or -alkenyl, branched ($C_1$–$C_4$) alkyl, ($C_3C_7$) cycloalkyl or -cycloalkenyl, halo, hydroxy, or acetyl; and Z is one of the groups defined in paragraphs (a) through (f). Compounds of formula (7) are useful as fungicides, in some cases as insecticides and miticides, and also as intermediates in preparation of compounds of formula (1).

The invention also provides novel compounds of the formula (8)

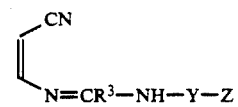

(8)

where R 

and $R^3$ are as defined in formula (1);

Y is an alkylene chain two to six carbon atoms long, optionally including a carbocyclic ring, and optionally including a hetero atom selected from O, $NR^4$, S, SO, $SO_2$, or $SiR^7R^8$, where $R^4$, $R^7$, and $R^8$ are as defined above, and optionally substituted with ($C_1$–$C_4$) alkyl, ($C_2$–$C_4$) alkenyl or -alkenyl, branched ($C_3$–$C_7$) alkyl, ($C_3$–$C_7$) cycloalkyl or -cycloalkenyl, halo, hydroxy, or acetyl; and Z is one of the groups defined in paragraphs (a) through (f). Compounds of formula (8) are useful as intermediates in preparation of compounds of formula (1) and (7).

The fungicide combinations of the invention comprise at least 1% by weight of a compound of formula (1) or (7) in combination with a second plant fungicide.

The fungicide compositions of the invention comprise a disease inhibiting and phytologically acceptable amount of compound of formula (1) or (7) in combination with a phytologically-acceptable carrier. Such compositions may optionally contain additional active ingredients, such as an additional fungicidal, miticidal, or insecticidal ingredient.

The fungicidal method of the invention comprises applying to the locus of a plant pathogen a disease inhibiting and phytologically acceptable amount of a compound of formula (1) or (7).

The insecticide and miticide combinations of the invention comprise at least 1% by weight of a compound of formula (1) or (7) in combination with a second insecticide or miticide.

The insecticide and miticide compositions of the invention comprise an insect- or mite-inactivating amount of a compound of formula (1) or (7) in combination with a carrier. Such compositions may optionally contain additional active ingredients, such as an additional fungicidal, miticidal, or insecticidal ingredient. The insecticidal or miticidal method of the invention comprises applying to a locus of an insect or mite an insect- or mite-inactivating amount of a compound of formula (1) or (7), or of a combination described above.

DETAILED DESCRIPTION OF THE INVENTION

Throughout this document, all temperatures are given in degrees Celsius, and all percentages are weight percentages unless otherwise stated.

The term "halo" refers to a F, Cl, or Br atom.

The term "$(C_1-C_7)$ alkoxy" refers to straight or branched chain alkoxy groups.

The term "$(C_1-C_7)$ alkylthio" refers to straight and branched chain alkylthio groups.

The term "halo $(C_1-C_7)$ alkyl" refers to a $(C_1-C_7)$ alkyl group, straight chain or branched, substituted with one or more halo atoms.

The term "halo $(C_1-C_7)$ alkoxy" refers to a $(C_1-C_7)$ alkoxy group substituted with one or more halo groups.

The term "halo $(C_1-C_4)$ alkylthio" refers to a $(C_1-C_4)$ alkylthio group, straight chain or branched, substituted with one or more halo atoms.

The term "substituted phenyl" refers to phenyl substituted with up to three groups selected from halo, I, $(C_1-C_{10})$ alkyl, branched $(C_3-C_6)$ alkyl, halo $(C_1-C_4)$ alkyl, hydroxy $(C_1-C_4)$ alkyl, $(C_1-C_4)$ alkoxy, halo $(C_1-C_4)$ alkoxy, phenoxy, substituted phenoxy, phenyl, substituted phenyl, $NO_2$, OH, CN, $(C_1-C_4)$ alkanoyloxy, or benzyloxy. The terms "substituted naphthyl", "substituted pyridyl" and "substituted indolyl" refer to these ring systems substituted with halo, halo $(C_1-C_4)$ alkyl, CN, $NO_2$, $(C_1-C_4)$ alkyl, $(C_1-C_4)$ branched alkyl, phenyl, $(C_1-C_4)$ alkoxy, or halo $(C_1-C_4)$ alkoxy.

The term "substituted phenoxy" refers to phenoxy substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, substituted phenoxy, phenyl, substituted phenyl, $NO_2$, OH, CN, $(C_1-C_4)$ alkanoyloxy, or benzyloxy.

The term "carbocyclic ring" refers to a saturated or unsaturated carbocyclic ring containing three to seven carbon atoms.

The terms "substituted phenylthio" and "substituted phenyl sulfonyl" refer to such groups substituted with up to three groups selected from halo, I, $(C_1-C_{10})$ alkyl, branched $(C_3-C_6)$ alkyl, halo $(C_1-C_7)$ alkyl, hydroxy $(C_1-C_7)$ alkyl, $(C_1-C_7)$ alkoxy, halo $(C_1-C_7)$ alkoxy, phenoxy, substituted phenoxy, phenyl, substituted phenyl, $NO_2$, OH, CN, $(C_1-C_4)$ alkanoyloxy, or benzyloxy.

The term "unsaturated hydrocarbon chain" refers to a hydrocarbon chain containing one or two sites of unsaturation.

The term "HPLC" refers to a high pressure liquid chromatography.

The term "bivalent hydrocarbon radical" refers to bivalent radicals derived from normal alkanes by removal of hydrogen atoms from each of the two terminal carbon atoms of the chain, e.g. methylene, ethylene, trimethylene, tetramethylene, etc.

COMPOUNDS

Compounds of formula (1) include furo(2,3-d)pyrimidines of formula (1a):

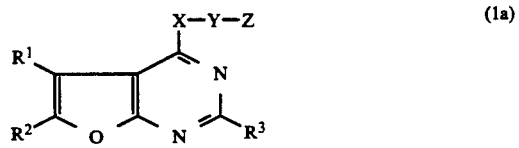
(1a)

furo(3,2-d)pyrimidines of formula (1b)

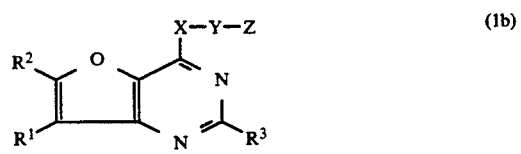
(1b)

and furo(3,4-d)pyrimidines of formula (1c)

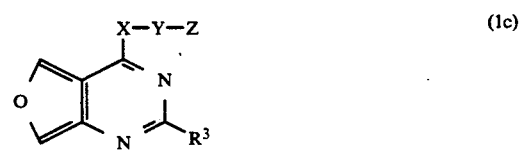
(1c)

While all of the compounds of the invention are useful fungicides, certain classes are preferred for reasons of greater efficacy or ease of synthesis, viz:

a) furo[2,3-d]pyrimidines of formula (1a);
b) 5-methylfuro[2,3-d]pyrimidines of formula (1a);
c) 6-methylfuro[2,3-d]pyrimidines of formula (1a);
d) 5,6-dimethylfuro[2,3-d]pyrimidines of formula (1a);
e) compounds of formula (1) wherein Y is an alkylene chain two to six carbon atoms long;
f) compounds of formula (1) wherein Y is $-(CH_2)_2-$;
g) compounds of formula (1) wherein Z is
h) compounds of formula (1) wherein Z is a substituted phenyl group of formula (2);
i) compounds of formula (1) wherein Z is a phenyl group of formula (2) in which one of the substituents $R^9$ to $R^{13}$ is a haloalkoxy group;
j) compounds of formula (1) wherein Z is 2-naphthyl;
k) compounds of formula (1) wherein Z is 3-$(C_1-C_4)$alkoxyphenyl;
l) compounds of formula (1) wherein E is 3-methoxyphenyl;
m) compounds of formula (1) wherein Z is 4-$(C_1-C_4)$alkoxyphenyl;
n) compounds of formula (1) wherein Z is 4-methoxyphenyl;
o) compounds of formula (1) wherein Z is 3-(halo($C_1$-$C_4$)alkyl)phenyl;
p) compounds of formula (1) wherein Z is 3-(trifluoromethyl)phenyl;
q) compounds of formula (1) wherein E is 4-(halo($C_1$-$C_4$)alkyl)phenyl;

r) compounds of formula (1) wherein Z is 4-(trifluoromethyl)phenyl;
s) compounds of formula (1) wherein E is 4-(1,1,2,2-tetrafluoroethoxy)phenyl;

t) compounds of formula (1) wherein Z is phenyl substituted with a branched $(C_3-_7)$alkyl group;
u) compounds of formula (1) wherein Z is 4-(t-butyl)phenyl;
v) compounds of formula (1) wherein Z is phenyl substituted with a $(C_1-C_4)$alkyl group;
w) compounds of formula (1) wherein Z is 4-(n-butyl)phenyl;
x) compounds of formula (1) wherein Z is phenyl substituted with a halo atom;
y) compounds of formula (1) wherein Z is 4-chlorophenyl;
z) compounds of formula (1) wherein Z is 4-fluorophenyl.

SYNETHESIS

The compounds of this invention are made using well known chemical procedures. The required starting materials are commercially available, or they are readily synthesized using standard procedures.

SYNETHESIS OF COMPOUNDS WHEREIN X IS $NR^4$

Compounds of formula (1) wherein X is NH are represented by the following formula (1d):

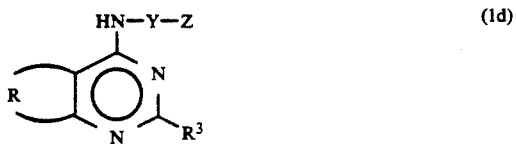

wherein each of the variable substituents are as defined above the formula (1). Compounds of formula (1d) wherein $R^3$ is H can be prepared by the procedure shown in the following Scheme 1:

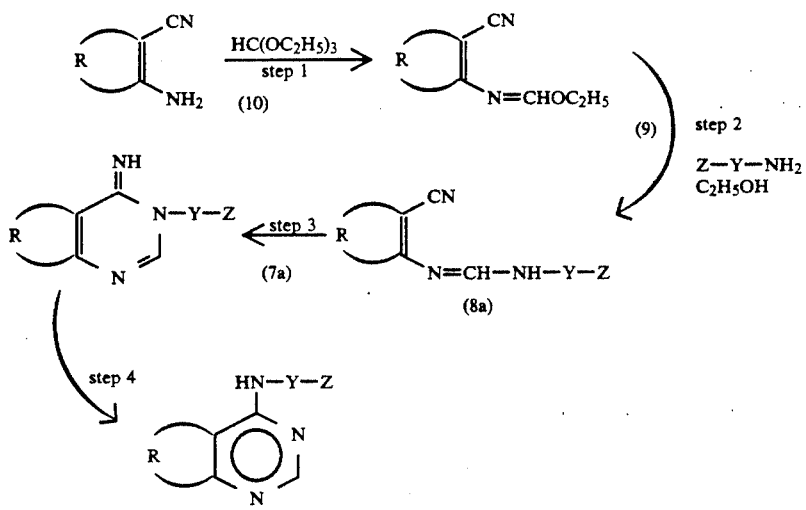

Scheme 1 represents an application of the general procedure that is described in Edward C. Taylor and Alexander McKillop, *The Chemistry of Cyclic Enaminonitriles and o-Aminonitriles* (Interscience 1970). Application of this procedure to preparation of furo[2,3-d]pyrimidines is described in *Chemical Abstracts* 80:96102f (1974), in U.S. Pat. No. 4,199,584 to Cox et al., and in *Chemica Scripta* 26, 337–342 (1986).

In step 1 of Scheme 1 an o-aminonitrile (10) is condensed with an orthoester of the formula $HC(OC_2H_5)_3$ or $HC(OCH_3)_3$. The reaction is optionally carried out in the presence of acetic anhydride.

In step 2 of Scheme 1, the imino ether (9) produced in step 1 is reacted with a primary amine of the formula $NH_2-Y-Z$, where Y and Z are as defined in formula (1). The preferred solvent is ethyl alcohol. If step 2 is carried out at room temperature, the novel o-cyanoamidine of formula (8) can be isolated. At elevated temperatures cyclization of the o-cyanoamidine (step 3) proceeds, delivering the imine of formula (7).

In Step 4, Dimroth rearrangement of the imine of formula (7) provides the N-substituted-4-amine of formula (1d). Rearrangement is favored by basic conditions or elevated temperatures.

o-Aminonitriles of formula (10), used as starting materials in Scheme 1, are prepared using known procedures, e.g., those described in *Acta Chemica Scandinavica* B29 224–232 (1975) (3-amino-2-cyanofurans);

Compounds of formula (1d) wherein $R^3$ is other than H can be prepared by the general procedure described in *Chemica Scripta* 25, 227–229 (1985), as illustrated in Scheme 2:

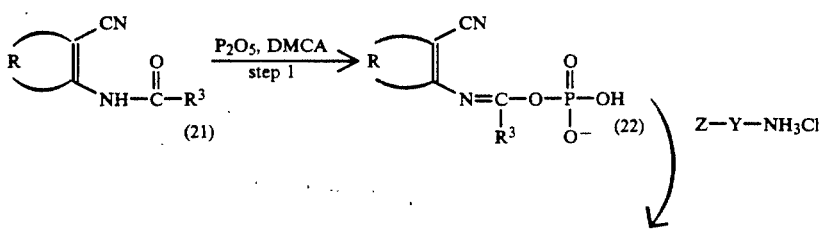

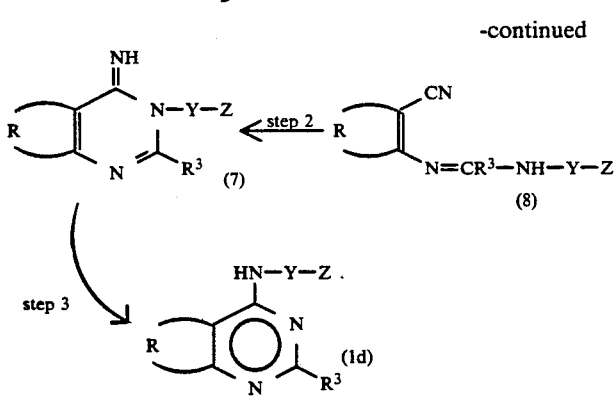

In step 1 and Scheme 2, the o-(acylamino)nitrile of formula (21) is reacted with phosphorus pentoxide, a tertiary amine such as triethylamine or N,N-dimethylcyclohexylamine (DMCA), and an amind hydrochloride of the formula Z—Y—NH$_3$·HCl to give the amidine intermediate of formula (8), which can cyclize, as in Scheme 1 to give the imino compound of formula (7). Upon heating, particularly in the presence of base, the imino compounds rearranged to provide the N-substituted-4-amino compounds of formula (1d) (step 3).

Compounds of formula (1) wherein X is NH can also be prepared by the process disclosed in *Chemica Scripta* 26, 337-342 (1986), illustrated in Scheme 3.

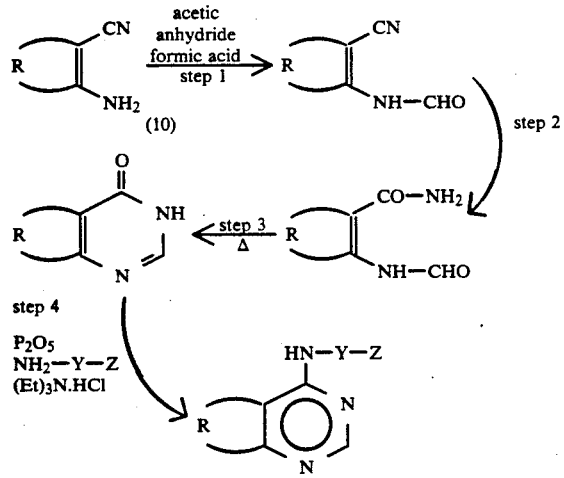

Compounds of formula (1) wherein X is NR$^4$ and R$^4$ is H or (C$_1$-C$_4$) alkyl may also be prepared by aminating a suitably substituted intermediate of the formula (b 23)

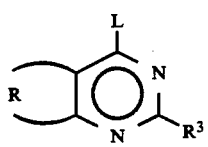

where L is a leaving group, such as F, Cl, Br, I, NO$_2$, 1,2,4-triazol-1-yl, O-SiMe$_3$, arylthio, alkylthio, alkylsulfonyl, arylsulfonyl, alkoxy, or arylsulfinyl. The general procedure is described in, e.g. *Bull. Soc. Chim. Fr.* 12, 4344 (1969); *Diss. Abstr. Int. B*32 (12), 6915 (1972); and Ger. Offen. 1,817,146; U.S. Pat. No. 4,199,584 to Cox, and U.S. Pat. No. 4,007,187 to Fauran et al. A chloride of formula (23) wherein L is Cl is allowed to react with an appropriate amine at a wide variety of temperatures (20°-180° C.), preferably in the presence of an acid acceptor, such as triethylamine. The reaction may be carried out neat, or in a non-reactive organic solvent. Compounds where R$^4$ is acyl are prepared from amines where R$^4$ is H, which were allowed to react with an acylating agent such as acetyl chloride or acetic anhydride.

Preparation of 4-chloro compounds of formula (23) is illustrated in U.S. Pat. Nos. 3,632,763 and 3,577,420.

SYNTHESIS OF COMPOUNDS WHEREIN X IS O

The compounds of formula (1) wherein X is 0 are made by condensing a compound of formula (23) with an alcohol or phenol of the formula (24):

HO—Y—Z (24)

where Y and Z are as previously defined.

The reaction is preferably carried out in the presence of a strong base, such as sodium hydride, in a non-reactive organic solvent, such as DMF, at a temperature in the range of 0° to 25° C. S Compounds wherein X is S are made by the same procedure using corresponding mercaptans of formula HS—Y—Z.

SYNTHESIS OF COMPOUNDS WHEREIN X IS CH$_2$

The compounds of formula (1) wherein X is CH$_2$ can be made using the process described in the *J. Heterocyclic Chemistry*, Vol. 14, 1081-1083 (1977).

This procedure involves hydrolysis and decarboxylation of 5-substituted-5-(4-furopyrimidyl)-barbituric acids of the formula

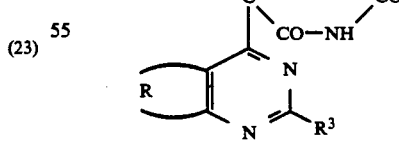

wherein the variable substituents are as defined for formula (1). The 5-substituted-5-(4-furopyrimidyl)barbituric acid is dissolved in a solution of sodium hydroxide and water and refluxed. The solution is then made slightly acidic and again refluxed.

Compounds of formula (1) wherein X is CRsRs may also be prepared by reacting a compound of formula (23) where L is H with a Grignard reagent of the formula Z—Y—CR$^5$R$^6$—MgX' or a lithio reagent of the formula Z—Y—CR$^5$R$^6$—Li, where X' is halo, to provide a 3,4-dihydrofuropyrimidine which is then oxidized to provide a compound of the invention. Typical reaction conditions are those described in Armarego and Smith, *J. Chem. Soc.*, page 5360 (1965).

The acid addition salts and N-oxides of compounds of formula (1) are obtained in the usual way.

Accordingly, the invention also provides a process for preparing a compound of formula (1) which comprises (a) condensing a compound of formula (23)

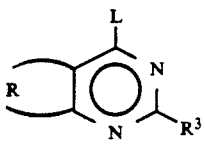

wherein R is as previously defined, and L is a leaving group, with an alcohol of the formula (8):

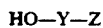 (8)

wherein Y and Z are as previously defined to produce a compound of formula (1) wherein X is O; or (b) condensing a compound of formula (23) as defined above with an amine of the formula (9)

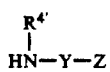 (9)

where R$^{4'}$ is H or (C$_1$-C$_4$) alkyl, and Y and Z are as previously defined, to provide a compound of formula (1) where X is NR$^{4'}$; or (c) acylating a compound of formula (1) wherein X is NH to provide a compound of formula (1) wherein X is NR$^4$ and R$^4$ is acyl; or (d) reacting a compound of formula (23) wherein L is H with a Grignard reagent of formula Z—Y—CR$^5$R$^6$—MgX', where X' is halo and Z and Y are as defined above, or with a lithio reagent of formula Z—Y—CR$^5$R$^6$—Li, to provide a 3,4-dihydro furopyrimidine, which is then oxidized to produce a compound of formula (1) wherein X is CR$^5$R$^6$; or (e) hydrolyzing and decarboxylating a 5-substituted-5-(4-(furopyrimidinyl)barbituric acid of the formula

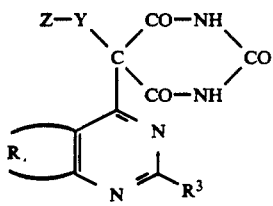

wherein R, R$^3$, R$^5$, R$^6$, Y, and Z are as previously defined to provide a compound of formula (1) wherein X is CR$^5$R$^6$; or (f) heating a compound of the formula (7)

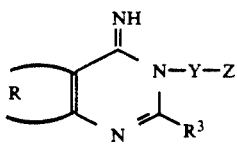

optionally in the presence of base to provide a compound of the formula (b 1d)

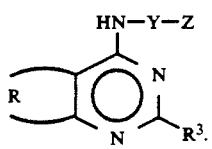

EXAMPLES 1-81

The following examples are compounds actually prepared by the above described general procedures. The melting point is given for each compound. In addition, although the data has not been included, each compound was fully characterized by one or more of NMR, IR, mass spectra, and combustion analysis. Specific illustrative preparations for the compounds of representative compounds follow the tabular listing.

| EXAMPLE NUMBER | COMPOUND | M.P. |
|---|---|---|
| 1 | N-[2-(4-methoxyphenyl)ethyl]-5,6-dimethylfuro[2,3-d]pyrimidin-4-amine | 150-151° C. |
| 2 | 5-methyl-N-[2-(4-methoxyphenyl)ethyl]furo[2,3-d]pyrimidin-4-amine | 154° C. |
| 3 | 5,6-dimethyl-N-[2-(4-ethoxyphenyl)ethyl]furo[2,3-d]pyrimidin-4-amine | 151° C. |
| 4 | N-[2-(4-methoxyphenyl)ethyl]-6-methylfuro[2,3-d]pyrimidin-4-amine | 186° C. |
| 5 | 6-methyl-4-(4-fluorophenoxy)furo-[2,3-d]pyrimidine | 105° dec. |
| 6 | 6-methyl-N-[2-(4-chlorophenyl)ethyl]-furo[2,3-d]pyrimidin-4-amine | 180° C. |
| 7 | 4-[2-(1,1'-biphenyl)-4-ylethoxy]6-methylfuro[2,3-d]pyrimidine | 124-125° C. |
| 8 | 6-methyl-N-[2-[3-(trifluoromethyl)-phenyl]ethyl]furo[2,3-d]pyrimidin-4-amine | 119° C. |
| 9 | 6-methyl-N-[2-(4-ethoxyphenyl)ethyl]-furo[2,3-d]pyrimidin-4-amine | 164° C. |
| 10 | N-[2-(4-chlorophenyl)ethyl]-5,6-dimethylfuro[2,3-d]pyrimidin-4-amine | 145° C. |
| 11 | 5-methyl-N-[2-(4-chlorophenyl)ethyl]-furo[2,3-d]pyrimidin-4-amine | 140° C. |
| 12 | 5,6-dimethyl-N-(2-phenylethyl)-furo[2,3-d]pyrimidin-4-amine | 135° C. |
| 13 | 5,6-dimethyl-4-[3-(3-pyridinyl)-propoxy]furo[2,3-d]pyrimidine | 75° C. |
| 14 | 5,6-dimethyl-N-[2-[[(2-chloro-6-fluorophenyl)methyl]thio]ethyl]-furo[2,3-d]pyrimidip-4-amine | 147° C. |
| 15 | N-[2-(4-methoxyphenyl)ethyl]furo-[2,3-d]pyrimidin-4-amine | 135-136° C. |
| 16 | 5-methyl-N-[2-[[(2-chloro-6-fluorophenyl)methyl]thio]ethyl]-furo[2,3-d]pyrimidin-4-amine | 167° C. |
| 17 | 5,6-dimethyl-4-(1-azabicyclo[2.2.2]-oct-3-yloxy)furo[2,3-d]pyrimidine | 105° C. |
| 18 | N-[2-(decahydro-2-naphthyl)ethyl]-5,6-dimethylfuro[2,3-d]pyrimidin-4-amine | 138° C. |
| 19 | 5-methyl-N-(2-phenylethyl)furo-[2,3-d]pyrimidin-4-amine | 132-133° C. |
| 20 | N-[2-[4-(t-butyl)phenyl]ethyl]-5,6-dimethylfuro[2,3-d]pyrimidin-4-amine | 148-150° C. |
| 21 | 5-methyl-N-[2-(2-naphthyl)ethyl]- | 141-142° C. |

-continued

| EXAMPLE NUMBER | COMPOUND | M.P. |
|---|---|---|
| 22 | furo[2,3-d]pyrimidin-4-amine 5,6-dimethyl-N-[2-(2-naphthyl)ethyl]-furo[2,3-d]pyrimidin-4-amine | 125° C. |
| 23 | 5,6-dimethyl-N-[2-[3-(trifluoromethyl)phenyl]ethyl]furo[2,3-d]pyrimidin-4-amine | 139–140° C. |
| 24 | 5,6-dimethyl-N-[2-(4-methylphenyl)ethyl]furo[2,3-d]pyrimidin-4-amine | 140° C. |
| 25 | 5,6-dimethyl-N-[2-(3,4-dimethoxyphenyl)ethyl]furo[2,3-d]pyrimidin-4-amine | 171° C. |
| 26 | N-[2-(4-chlorophenyl)-3-(4-fluorophenyl)propyl]-5,6-dimethylfuro-[2,3-d]pyrimidin-4-amine | 147° C. |
| 27 | N-[2-(3,4-dimethoxyphenyl)ethyl]-5-methylfuro[2,3-d]pyrimidin-4-amine | 164° C. |
| 28 | 5,6-dimethyl-4-(2-methoxyphenoxy)furo[2,3-d]pyrimidine | 121–122° C. |
| 29 | 5,6-dimethyl-4-(2-methylphenoxy)furo[2,3-d]pyrimidine | 78–79° C. |
| 30 | N-[2-(4-methoxyphenyl)ethyl]-5,6,-7,8-tetrahydrobenzofuro[2,3-d]-pyrimidin-4-amine | 135° C. |
| 31 | 6-methyl-N-[2-(2-naphthalenyl)ethyl]furo[2,3-d]pyrimidin-4-amine | 127° C. |
| 32 | 5,6-dimethyl-4-[4-(trifluoromethoxy)phenoxy]furo[2,3-d]pyrimidine | 105–106° C. |
| 33 | 5-methyl-N-[2-(3-methoxyphenyl)ethyl]furo[2,3-d]pyrimidin-4-amine | 116° C. |
| 34 | 4-(4-fluorophenoxy)-5,6,7,8-tetrahydrobenzofuro[2,3-d]pyrimidine | 96–97° C. |
| 35 | 5-methyl-N-[2-(2-methoxyphenyl)ethyl]furo[2,3-d]pyrimidin-4-amine | 122° C. |
| 36 | 4-[(5,6-dimethylfuro[2,3-d]pyrimidin-4-yl)oxy]benzonitrile | N/A |
| 37 | 2-[(5,6-dimethylfuro[2,3-d]pyrimidin-4-yl)oxy]benzonitrile | 225° C. |
| 38 | 6-methyl-4-[2-(1-adamantyl)ethoxy]furo[2,3-d]pyrimidine | 99–100° C. |
| 39 | 6-methyl-4-[2-[4-(phenylmethoxy)phenyl]ethoxy]furo[2,3-d]pyrimidine | 90° C. |
| 40 | 6-methyl-4-[2-(4-methoxyphenyl)ethoxy]furo[2,3-d]pyrimidine | 75° C. |
| 41 | 5,6-dimethyl-4-[2-[4-[4-(trifluoromethyl)phenoxy]phenyl]ethoxy]furo-[2,3-d]pyrimidine | oil |
| 42 | 6-methyl-4-[2-[4-(trifluoromethyl)phenyl]ethoxy]furo[2,3-d]pyrimidine | 73° C. |
| 43 | 6-methyl-4-[2-[4-(t-butoxy)phenyl]ethoxy]furo[2,3-d]pyrimidine | 75° C. |
| 44 | 4-[2-(4-butoxyphenyl)ethoxy]-6-methylfuro[2,3-d]pyrimidine | 60–61° C. |
| 45 | 5,6-dimethyl-4-[2-[4-(n-butoxy)phenyl]ethoxy]furo[2,3-d]pyrimidine | 60° C. |
| 46 | 4-[2-[4-(1,1-dimethylethyl)phenyl]-ethoxy]-6-methylfuro[2,3-d]pyrimidine | N/A |
| 47 | N-[2-[4-(1,1,2,2-tetrafluoroethoxy)phenyl]ethyl]-5,6-dimethylfuro[2,3-d]-pyrimidin-4-amine | 111° C. |
| 48 | 5-methyl-N-[2-(4-methylphenyl)ethyl]furo[2,3-d]pyrimidin-4-amine | 139° C. |
| 49 | 5,6-dimethyl-4-(4-fluorophenoxy)furo[2,3-d]pyrimidine | 126° C. |
| 50 | 4-[2-[4-(t-butyl)phenyl]ethoxy]-5,6-dimethylfuro[2,3-d]pyrimidine | 107–108° C. |
| 51 | 4-[2-[4-biphenylyl]ethoxy]-5,6-dimethylfuro[2,3-d]pyrimidine | 83° C. |
| 52 | 4-[2-(4-methoxyphenyl)ethoxy]-5,6-dimethylfuro[2,3-d]pyrimidine | 69–70° C. |
| 53 | 4-[2-(4-chlorophenyl)ethoxy]-5,6-dimethylfuro[2,3-d]pyrimidine | 84° C. |
| 54 | 5,6-dimethyl-4-[2-[4-(trifluoromethyl)phenyl]ethoxy]furo[2,3-d]pyrimidine | 74–75° C. |
| 55 | 5,6-dimethyl-4-[2-(2-naphthyl)ethoxy]furo[2,3-d]pyrimidine | 85° C. |
| 56 | 5,6-dimethyl-4-[(4-fluorophenyl)thio]furo[2,3-d]pyrimidine | 115° C. |
| 57 | Cis-5,6-dimethyl-4-[2-(2,6-dimethyl- | 71–74° C. |

-continued

| EXAMPLE NUMBER | COMPOUND | M.P. |
|---|---|---|
|  | 4-morpholinyl)ethoxy]furo[2,3-d]-pyrimidine |  |
| 58 | Trans-5,6-dimethyl-4-[2-(2,6-dimethyl-4-morpholinyl)ethoxy]furo-[2,3-d]pyrimidine | 71–74° C. |
| 59 | 4-(2-chloro-4-fluorophenoxy)-5,6-dimethylfuro[2,3-d]pyrimidine | 164–165° C. |
| 60 | 5,6-dimethyl-4-[(2-methyloxan-5-yl)methoxy]furo[2,3-d]pyrimidine | 49–50° C. |
| 61 | 5,6-dimethyl-4-[2-(2-thienyl)ethoxy]furo[2,3-d]pyrimidine | 72° C. |
| 62 | 5,6-dimethyl-4-(4-methylphenoxy)-furo[2,3-d]pyrimidine | 103° C. |
| 63 | 5,6-dimethyl-4-[3-(trifluoromethyl)phenoxy]furo[2,3-d]pyrimidine | 125° C. |
| 64 | 5,6-dimethyl-4-phenoxyfuro[2,3-d]pyrimidine | 74° C. |
| 65 | 5,6-dimethyl-4-(4-methoxyphenoxy)-furo[2,3-d]pyrimidine | 125–126° C. |
| 66 | 4-(2-fluorophenoxy)-5,6-dimethyl-furo[2,3-d]pyrimidine | 87° C. |
| 67 | 4-[2-[4-(2,2-dimethylethyl)phenyl]-2-methylethoxy]5,6-dimethylfuro-[2,3-d]pyrimidine | oil |
| 68 | 5,6-dimethyl-N-[2-[4-(trifluoromethoxy)phenyl]ethyl]furo[2,3-d]-pyrimidin-4-amine | N/A |
| 69 | 5,6-dimethyl-4-[2-[4-(trifluoromethoxy)phenyl]ethoxy]furo[2,3-d]pyrimidine | 78° C. |
| 70 | 5,6-dimethyl-4-[2-[3,4-difluoromethylenedioxy)phenyl]ethoxy]furo-[2,3-d]pyrimidine | 95° C. |
| 71 | 5,6-dimethyl-N-[3-[4-(n-hexyloxy)-phenyl]-2-(1-naphthyl)propyl]furo-[2,3-d]pyrimidin-4-amine | 105° C. |
| 72 | 5,6-dimethyl-N-[2-(1-cyclohexenyl)-ethyl]furo[2,3-d]pyrimidin-4-amine | 124° C. |
| 73 | 5,6-dimethyl-N-[2-[4-(2,2,2-trifluoroethoxy)phenyl]ethyl]furo[2,3-d]-pyrimidin-4-amine | 155–156° C. |
| 74 | 5,6-dimethyl-4-[2-[4-(1-ethyl-1-methylbutoxy)phenyl]ethoxy]furo-[2,3-d]pyrimidine | oil |
| 75 | 5,6-dimethyl-4-[2-[4-[benzo[b]-1,4-dioxan-6-yl]ethoxy]furo[2,3-d]-pyrimidine | 146° C. |
| 76 | 5,6-dimethyl-4-[2-[2-(trifluoromethyl)-phenyl]ethoxy]furo[2,3-d]pyrimidine | 84° C. |
| 77 | 5,6-dimethyl-N-[1,1-dimethyl-2-phenylethyl]furo[2,3-d]pyrimidin-4-amine | 59° C. |
| 78 | 5,6-dimethyl-4-[4-(2,2,2-trifluoroethoxy)phenyl]ethoxy]furo[2,3-d]-pyrimidine | 72–73° C. |

The following detailed examples illustrate the procedures used to prepare the compounds of formula (1).

EXAMPLE 2

5-Methyl-N-2-(4-methoxyphenyl)ethyl]furo[2,3-d]pyrimidin-4-amine

A mixture of 4 g of 2-amino-3-cyano-4-methylfuran, 3 mL of triethylorthoformate and 0.5 mL of acetic anhydride was heated at 135° C. for three hours. To the hot solution was added 4.5 g of 2-(4-methoxyphenyl)ethylamine, 5 mL of acetic anhydride, and 3.1 g of sodium acetate. The temperature of the mixture was kept at 135° C. for three additional hours, then the mixture was cooled and combined with a mixture of water and ether. The ether layer was separated, and product was extracted from the remaining aqueous layer with large volumes of ether. The ether extracts were combined, dried over magnesium sulfate, filtered, and concentrated. The residue was recrystallized from acetone/ether. Yield 2.6 g. M.P. 184° C.

EXAMPLE 8

6-Methyl-N-[2-3-(trifluoromethyl)phenyl]ethyl]-furo[2,3-d]pyrimidin-4-amine

A mixture of 1.9 g of 2-[3-(trifluoromethyl)phenyl]ethylamine and 1.6 g of 4-chloro-6-methylfuro[2,3-d]pyrimidine was heated for ten minutes at 230° C. The mixture was then cooled and the product extracted in ethyl acetate/water. The organic phase was separated, washed with water, dried over magnesium sulfate, filtered, and concentrated The residue was chromatographed on a silica column using toluene and acetone as eluent. Yield 0.97 g. M.P. 119° C.

EXAMPLE 11

5-Methyl-N-[2-(4-chlorophenyl)ethyl]furo[2,3-d]pyrimidin-4-amine

A mixture of 4.0 g of 2-amino-3-cyano-4-methylfuran, 3 cc of triethylorthoformate, and 0.05 cc of acetic anhydride was heated to 135° C. for three hours. Then 5 g of 2-(4-chlorophenyl)ethylamine, 5 cc of glacial acetic acid, and 3.2 g of sodium acetate were added to the reaction mixture. The temperature of the mixture was maintained at 135° C. for three additional hours, after which the mixture was cooled, treated with water and extracted with dichloromethane. The organic phase was then concentrated and washed with water. The solids were extracted from the organic phase with large volumes of ether, which were combined and concentrated to provide 1.07 g of product. M.P. 140° C.

EXAMPLE 15

N-[2-(4-methoxyphenyl)ethyl]furo[2,3-d]pyrimidin-4-amine a. A mixture of 5.8 g of malononitrile, 4.8 mL of triethylamine, and 3.8 g of glycoaldehyde was refluxed for 10 minutes in 100 cc of toluene. Then the mixture was cooled and the toluene layer decanted. The dark residue was extracted with fresh toluene several additional times. The extracts were combined, washed with water, dried over magnesium sulfate, and concentrated under vacuum to produce 2-amino-3-cyanofuran as an oil.

b. The 2-amino-3-cyanofuran produced in the preceding step was combined with 4.2 mL of triethylorthoformate, and 0.5 mL of acetic anhydride, and the mixture was heated to 130° C. for two hours. Then was added 1.8 g of sodium acetate and 3 g of 2-(4-methoxyphenyl-)ethylamine, followed by 3 mL of acetic acid. The resulting mixture was heated for two hours at 130°-138° C., then cooled and diluted with water. The product was extracted with large volumes of ether. The ether extracts were combined, washed with water, dried over magnesium sulfate, and concentrated. The residue was recrystallized from ether and petroleum ether. Yield 0.65 g. M.P. 135°-136° C.

EXAMPLE 43

4-[2-4-(t-butox-y)phenyl]ethoxy-6-methylfuro[2,3-d]pyrimidine

To a dispersion of 0.3 g of 60% sodium hydride in mineral oil in 25 mL of DMF was added 1.13 g of 2-[4-(t-butoxy)phenyl]ethanol, and the mixture was agitated for two hours. Then 0.9 g of 4-chloro-6-methyl-furo[2,3d]pyrimidine was added, and the mixture was agitated at room temperature overnight, after which the mixture was poured on ice. Gray solids precipitated and were collected by filtration and dried. Yield 0.76 g. M.P. 75° C.

EXAMPLE 44

4-[2-[4-(n-butoxy)phenyl]ethoxy]-6-methylfuro[2,3-d]pyrimidine

To a dispersion of 0.52 g of sodium hydride in 35 mL of DMF was added 2 g of 2-4-(n-butoxy)phenyl]ethanol at room temperature to provide the sodium salt of the alcohol. To this mixture was added 6.5 g of 4-chloro-6-methylfuro[2,3-d]pyrimidine, and the resulting mixture was agitated at room temperature overnight, then poured on ice. Pale yellow solid precipitated and were isolated by filtration, dried, and recrystallized first from ether, and then from a mixture of ether and petroleum ether. Yield 1.2 g. M.P. 60°-61° C.

EXAMPLE 52

4-[2-(4-methoxyphenyl)ethoxy]-5,6-dimethylfuro[2,3-d]pyrimidine

To a dispersion of 0.48 g of 60% sodium hydride in mineral oil in 50 mL of DMF was added 1.5 g of 2-(4methoxyphenyl)ethanol to produce the sodium salt of the alcohol. To this mixture was added 1.2 g of 4-chloro-5,6-dimethylfuro[2,3-d]pyrimidine in small portions at room temperature and the dispersion was allowed to react overnight. The reaction mixture was concentrated under vacuum and the residue dispersed in water. The product was extracted into large volumes of ether, which were combined, dried over magnesium sulfate, filtered, and concentrated. The residue was recrystallized from ether and petroleum ether. M.P. 69°-70° C.

The following compounds of formula (7) were prepared and isolated.

| EXAMPLE NUMBER | COMPOUND | M.P. |
| --- | --- | --- |
| 79 | 5-methyl-3-[2-(2-naphthyl)ethyl]-furo[2,3-d]pyrimidin-4(3H)-imine | 145° C. |
| 80 | 3-[2-(4-methoxyphenyl)ethyl]-5,6-dimethylfuro[2,3-d]pyrimidin-4(3H)-imine | 125° C. |
| 81 | 3-[2-[3-(trifluoromethyl)phenyl)-ethyl]-5,6-dimethylfuro[2,3-d]-pyrimidin-4(3H)-imine | 148-149° C. |

The following detailed preparation illustrates the general procedure used to prepare compounds of formula (7) (see also Schemes 1 and 2, supra).

EXAMPLE 80

3-[2-(4-methoxyphenyl)ethyl]-5,6-dimethylfuro[2,3-d]pyrimidin-4(3H)-imine

2-Amino-4,5-dimethyl-3-cyanofuran and trimethylorthoformate were refluxed for one hour. The solution was then concentrated under vacuum To the solution was added 3 g of 4-methoxy-phenethylamine dissolved in 10 mL of benzene. After setting overnight at room temperature, the mixture was concentrated under vacuum. The residue was dissolved in acetone/ether and cooled. A yellow precipitate formed, which was isolated, digested in ether and air dried. The solids were again digested in acetone/ether, and filtered. M.P. 125° C.

FUNGICIDE UTILITY

The compounds of the present invention have been found to control fungi, particularly plant pathogens. When employed in the treatment of plant fungal diseases, the compounds are applied to the plants in a disease inhibiting and phytologically acceptable amount. The term "disease inhibiting and phytologically acceptable amount," as used herein, refers to an amount of a compound of the invention which kills or inhibits the plant disease for which control is desired, but is not significantly toxic to the plant. This amount will generally be from about 1 to 1000 ppm, with 10 to 500 ppm being preferred. The exact concentration of compound required varies with the fungal disease to be controlled, the type formulation employed, the method of application, the particular plant species, climate conditions and the like. A suitable application rate is typically in the range from 0.25 to 4 lb/A. The compounds of the invention may also be used to protect stored grain and other non-plant loci from fungal infestation.

GREENHOUSE TESTS

The following experiments were performed in the laboratory to determine the fungicidal efficacy of the compounds of the invention.

TEST 1

This screen was used to evaluate the efficacy of the present compounds against a variety of different organisms that cause plant diseases.

The test compounds were formulated for application by dissolving 50 mg of the compound into 1.25 ml of solvent. The solvent was prepared by mixing 50 ml of "Tween 20" (polyoxyethylene (20) sorbitan monolaurate emulsifier) with 475 ml of acetone and 475 ml of ethanol. The solvent/compound solution was diluted to 125 ml with deionized water. The resulting formulation contains 400 ppm test chemical. Lower concentrations were obtained by serial dilution with the solvent-surfactant mixture.

The formulated test compounds were applied by foliar spray. The following plant pathogens and their corresponding plants were employed.

| Pathogen | Designation in Following Table | Host |
|---|---|---|
| Erysiphe graminis tritici (powdery mildew) | POWD MDEW | wheat |
| Pyricularia oryzae (rice blast) | RICE BLAS | rice |
| Puccinia recondita tritici (leaf rust) | LEAF RUST | wheat |
| Botrytis cinerea (gray mold) | GRAY MOLD | grape berries |
| Pseudoperonospora cubensis (downy mildew) | DOWN MDEW | squash |

The formulated technical compounds were sprayed on all foliar surfaces of the host plants (or cut berry) to past run-off. Single pots of each host plant were placed on raised, revolving pedestals in a fume hood. Test solutions were sprayed on all foliar surfaces. All treatments were allowed to dry and the plants were inoculated with the appropriate pathogens within 2–4 hours.

Table 1 presents the activity of typical compounds of the present invention when evaluated in this experiment. The effectiveness of test compounds in controlling disease was rated using the following scale.

0 = not tested against specific organism
− = 0–19% control at 400 ppm
+ = 20–89% control at 400 ppm
++ = 90–100% control at 400 ppm
+++ = g0–100% control at 100 ppm

| EXAMPLE NUMBER | POWD MDEW | RICE BLAST | LEAF RUST | GRAY MOLD | DOWN MDEW |
|---|---|---|---|---|---|
| 1 | − | ++ | + | − | + |
| 2 | + | ++ | +++ | − | +++ |
| 3 | − | + | + | − | + |
| 4 | − | + | ++ | − | − |
| 5 | + | − | ++ | − | − |
| 6 | − | − | − | − | − |
| 7 | − | + | − | − | + |
| 8 | + | + | +++ | − | +++ |
| 9 | − | − | ++ | − | + |
| 10 | − | ++ | + | − | + |
| 11 | + | ++ | +++ | − | ++ |
| 12 | − | + | ++ | − | ++ |
| 13 | − | − | − | − | − |
| 14 | − | − | − | − | − |
| 15 | + | + | ++ | − | +++ |
| 16 | − | − | − | − | − |
| 17 | − | − | − | − | − |
| 18 | − | − | − | + | − |
| 19 | + | − | +++ | − | +++ |
| 20 | − | + | +++ | − | +++ |
| 21 | ++ | − | +++ | − | +++ |
| 22 | − | − | − | − | − |
| 23 | − | − | + | − | − |
| 24 | − | + | ++ | − | − |
| 25 | − | − | + | − | − |
| 26 | − | − | − | − | − |
| 27 | − | − | ++ | − | ++ |
| 28 | − | − | − | − | − |
| 29 | + | + | + | − | + |
| 30 | − | − | + | − | + |
| 31 | + | + | +++ | − | +++ |
| 32 | − | − | − | 0 | − |
| 33 | ++ | + | +++ | 0 | +++ |
| 34 | − | − | + | 0 | − |
| 35 | − | − | ++ | 0 | + |
| 36 | − | − | − | 0 | − |
| 37 | − | − | − | 0 | + |
| 38 | − | − | − | − | − |
| 39 | − | − | ++ | − | − |
| 40 | + | − | ++ | − | ++ |
| 41 | ++ | + | +++ | − | +++ |
| 42 | + | + | ++ | − | ++ |
| 43 | ++ | + | ++ | − | +++ |
| 44 | − | − | ++ | − | + |
| 45 | + | − | +++ | − | + |
| 46 | − | − | − | − | − |
| 47 | + | +++ | +++ | − | +++ |
| 48 | ++ | ++ | +++ | − | ++ |
| 49 | ++ | − | ++ | − | − |
| 50 | + | + | + | − | + |
| 51 | − | − | − | − | ++ |
| 52 | ++ | ++ | +++ | − | +++ |
| 53 | + | + | ++ | − | − |
| 54 | ++ | ++ | ++ | − | − |
| 55 | − | − | + | − | − |
| 56 | + | + | + | − | − |
| 57 | − | − | − | − | + |
| 58 | − | − | + | − | + |
| 59 | ++ | − | + | − | − |
| 60 | − | − | − | − | ++ |
| 61 | ++ | + | + | − | ++ |
| 62 | ++ | − | − | − | − |
| 63 | − | − | − | − | + |
| 64 | ++ | − | + | − | ++ |
| 65 | + | − | − | − | − |
| 66 | ++ | − | + | − | ++ |
| 67 | + | ++ | + | + | + |
| 68 | + | ++ | + | − | ++ |
| 69 | ++ | + | + | − | − |
| 70 | − | − | − | − | − |

-continued

| EXAMPLE NUMBER | POWD MDEW | RICE BLAST | LEAF RUST | GRAY MOLD | DOWN MDEW |
|---|---|---|---|---|---|
| 71 | − | − | − | − | − |
| 72 | + | − | ++ | − | ++ |
| 73 | − | − | + | − | + |
| 74 | − | − | − | − | + |
| 75 | − | − | − | − | + |
| 76 | ++ | − | − | − | + |
| 77 | ++ | ++ | ++ | − | ++ |
| 79 | − | + | + | − | +++ |
| 80 | − | − | − | − | 0 |
| 81 | + | ++ | ++ | − | ++ |

PLANT PATHOLOGY SCREEN

COMBINATIONS

Fungal disease pathogens are known to develop resistance to fungicides. When strains resistant to a fungicide do develop, it becomes necessary to apply larger and larger amounts of the fungicide to obtain desired results. To retard the development of resistance to new fungicides, it is desirable to apply the new fungicides in combination with other fungicides. Use of a combination product also permits the product's spectrum of activity to be adjusted.

Accordingly, another aspect of the invention is a fungicidal combination comprising at least 1% by weight of a compound of formula (1) in combination with a second fungicide.

Contemplated classes of fungicides from which the second fungicide may be selected include:
1) N-substituted azoles, for example propiconazole, triademefon, flusilazol, diniconazole, ethyltrianol, myclobutanil, and prochloraz;
2) pyrimidines, such as fenarimol and nuarimol;
3) morpholines, such as fenpropimorph and
4) piperazines, such as triforine; and
5) pyridines, such as pyrifenox.

Fungicides in these five classes all function by inhibiting sterol biosynthesis. Additional classes of contemplated fungicides, which have other mechanisms of action include:
6) dithiocarbamates, such as maneb and mancozeb;
7) phthalimides, such as captafol;
8) isophthalonitrites, such as chlorothalonil;
9) dicarboximides, such as iprodione;
10) benzimidazoles, such as benomyl and carbendazim;
11) 2-aminopyrimidines, such as ethirimol;
12) carboxamides, such as carboxin; and
13) dinitrophenols, such as dinocap.

The fungicide combinations of the invention contain at least 1%, ordinarily 20 to 80%, and more typically 50 to 75% by weight of a compound of formula (1).

INSECTICIDE AND MITICIDE UTILITY

The compounds of the invention are also useful for the control of insects and mites. Therefore, the present invention also is directed to a method for inhibiting an insect or mite which comprises applying to a locus of the insect or mite an insect- or mite-inhibiting amount of a compound of formula (1).

The compounds of the invention show activity against a number of insects and mites. More specifically, the compounds show activity against melon aphid, which is a member of the insect order Homoptera. Other members of the Homoptera include leafhoppers, planthoppers, pear pyslla, apple sucker, scale insects, whiteflies, spittle bugs as well as numerous other host specific aphid species. Activity has also been observed against greenhouse thrips, which are members of the order Thysanoptera. The compounds also show activity against Southern armyworm, which is a member of the insect order Lepidoptera. Other typical members of this order are codling moth, cutworm, clothes moth, Indian-meal moth, leaf rollers, corn earworm, European corn borer, cabbage worm, cabbage looper, cotton bollworm, bagworm, eastern tent caterpillar, sod webworm, and fall armyworm.

Representative mite species with which it is contemplated that the present invention can be practiced include those listed below.

| FAMILY | SCIENTIFIC NAME | COMMON NAME |
|---|---|---|
| ACARIDAE | Aleurobius farinae | |
| | Rhizoglyphus echinopus | Bulb mite |
| | Rhizoglyphus elongatus | |
| | Rhizoglyphus rhizophagus | |
| | Rhizoglyphus sagittatae | |
| | Rhizoglyphus tarsalis | |
| ERIOPHYIDAE | Abacarus farinae | Grain rust mite |
| | Aceria brachytarsus | |
| | Acalitus essigi | Redberry mite |
| | Aceria ficus | |
| | Aceria fraaxinivorus | |
| | Aceria granati | |
| | Aceria parapopuli | |
| | Eriophyes sheldoni | Citrus bud mite |
| | Aceria tulipae | |
| | Aculus carnutus | Peach silver mite |
| | Aculus schlechtendali | Apple rust mite |
| | Colomerus vitis | Grape erineum mite |
| | Eriophyes convolvens | |
| | Eriophyes insidiosus | |
| | Eriophyes malifoliae | |
| | Eriophyes padi | |
| | Eriophyes pruni | |
| | Epitrimerus pyri | Pear leaf blister mite |
| | Eriophyes ramosus | |
| | Eriophyes sheldoni | Citrus bud mite |
| | Eriophyes ribis | |
| | Phyllocoptes gracilis | Dryberry mite |
| | Phyllocoptruta oleivora | Citrus rust mite |
| | Phytoptus ribis | |
| | Trisetacus pini | |
| | Vasates amygdalina | |
| | Vasates eurynotus | |
| | Vasates quadripedes | Maple bladd-ergall mite |
| | Vasates schlechtendali | |
| EUPODIDAE | Penthaleus major | Winter grain mite |
| | Linopodes spp. | |
| NALEPELLIDAE | Phylocoptella avellanae | Filbert bud mite |
| PENTHALEIDAE | Halotydeus destrustor | |
| PYEMOTIDAE | Pyemotes tritici | Straw itch mite |
| | Siteroptes cerealium | |
| TARSONEMIDAE | Polyphagotarsonemus latus | Broad mite |
| | Steneotarsonemus pallidus | Cyclamen mite |
| TENUIPALPIDAE | Brevipalpus californicus | |
| | Brevipalpus obovatus | Privet mite |
| | Brevipalpus lewisi | Citrus flat mite |
| | Dolichotetranychus | Pineapple |

-continued

| FAMILY | SCIENTIFIC NAME | COMMON NAME |
|---|---|---|
| | floridanus | flase spider mite |
| | Tenuipalpes granati | |
| | Tenuipalpes pacificus | |
| TETRANYCHIDAE | Bryobia arborea | |
| | Bryobia practiosa | Clover mite |
| | Bryobia rubrioculus | Brown mite |
| | Eotetranychus coryli | |
| | Eotetranychus hicoriae | Pecan deaf scorch mite |
| | Eotetranychus lewisi | |
| | Eotetranychus sexmaculatus | Sixspotted spider mite |
| | Eotetranychus willametti | |
| | Eotetranychus banksi | Texas citrus mite |
| | Oligonychus ilicis | Southern red mite |
| | Oligonychus pratensis | Banks grass mite |
| | Oligonychus ununguis | Spruce spider mite |
| | Panonychus citri | Citrus red mite |
| | Panonychus ulmi | European red mite |
| | Paratetranychus modestus | |
| | Paratetranychus pratensis | |
| | Paratetranychus viridis | |
| | Petrobia latens | Brown wheat mite |
| | Schizotetranychus celarius | Bamboo spider mite |
| | Schizotetranychus pratensis | |
| | Tetranychus canadensis | Fourspotted spider mite |
| | Tetranychus cinnabarinus | Carmine spider mite |
| | Tetranychus mcdanieli | McDaniel spider mite |
| | Tetranychus pacificus | Pacific spider mite |
| | Tetranychus schoenei | Schoene spider mite |
| | Tetranychus urticae | Twospotted spider mite |
| | Tetranychus turkestani | Strawberry spider mite |
| | Tetranychus desertorum | Desert spider mite |

The compounds are useful for reducing populations of insects and mites, and are used in a method of inhibiting an insect or mite population which comprises applying to a locus of the insect or arachnid an effective insect- or mite-inactivating amount of a compound of formula (1). The "locus" of insects or mites is a term used herein to refer to the environment in which the insects or mites live or where their eggs are present, including the air surrounding them, the food they eat, or objects which they contact. For example, plant-ingesting insects or mites can be controlled by applying the active compound to plant parts, which the insects or mites eat, particularly the foliage. It is contemplated that the compounds might also be useful to protect textiles, paper, stored grain, or seeds by applying an active compound to such substance. The term "inhibiting an insect or mite" refers to a decrease in the numbers of living insects or mites; or a decrease in the number of viable insect or mite eggs. The extent of reduction accomplished by a compound depends, of course, upon the application rate of the compound, the particular compound used, and the target insect or mite species. At least an insect-inactivating or mite-inactivating amount should be used. The terms "insect-inactivating amount" and "mite-inactivating amount" are used to describe the amount, which is sufficient to cause a measurable reduction in the treated insect or mite population. Generally an amount in the range from about 1 to about 1000 ppm active compound is used.

In a preferred embodiment, the present invention is directed to a method for inhibiting a mite which comprises applying to a plant an effective mite-inactivating amount of a compound of formula (1) in accordance with the present invention.

MITE/INSECT SCREEN

The compounds of examples were tested for miticidal and insecticidal activity in the following mite/ insect screen.

Each test compound was formulated by dissolving the compound in acetone/alcohol (50:50) mixture containing 23 g of "TOXIMUL R" (sulfonate/nonionic emulsifier blend) and 13 g of "TOXIMUL S" (sulfonate/nonionic emulsifier blend) per liter. These mixtures were then diluted with water to give the indicated concentrations.

Twospotted spider mites (*Tetranychus urticae* Koch) and melon aphids (*Aphis gossypii* Glover) were introduced on squash cotyledons and allowed to establish on both leaf surfaces. Other plants in the same treatment pot were left uninfested. The leaves were then sprayed with 5 ml of test solution using a DeVilbiss atomizing sprayer at 10 psi. Both surfaces of the leaves were covered until runoff, and then allowed to dry for one hour. Two uninfested leaves were then excised and placed into a Petri dish containing larval southern armyworm (*Spodopetra eridania* Cramer).

Activity on Southern corn rootworm (*Diabrotica undecimpuctata howardi* Barber) was evaluated by adding two ml of tap water, a presoaked corn seed, and 15 g of dry sandy soil to a one ounce plastic container. The soil was treated with 1 mL of test solution containing a predetermined concentration of test compound. After six to 12 hours of drying, five 2-3 instar corn rootworm larvae were added to the individual cups, which were then capped and held at 23° C.

After standard exposure periods, percent mortality and phytotoxicity were evaluated. Results for the compounds found to be active are reported in Table 3. The remaining compounds showed no activity. The following abbreviations are used in Table 3:
CRW refers to corn rootworm
SAW refers to Southern armyworm
SM refers to twospotted spider mites
MA refers to melon aphids.

| | MITE & INSECT SCREEN | | | | | |
|---|---|---|---|---|---|---|
| EXAMPLE NUMBER | CRW RATE PPM | CRW RESULTS % | SAW SM & MA RATE PPM | SAW RESULTS % | SM RESULTS % | MA RESULTS % |
| 1 | 12.00 | 0 | 200 | 0 | 0 | 80 |

-continued

| | | MITE & INSECT SCREEN | | | | |
|---|---|---|---|---|---|---|
| EXAMPLE NUMBER | CRW RATE PPM | CRW RESULTS % | SAW SM & MA RATE PPM | SAW RESULTS % | SM RESULTS % | MA RESULTS % |
| | 24.00 | 100 | 400 | 0 | 0 | 0 |
| 2 | 12.00 | 0 | 200 | 0 | 0 | 0 |
| | 24.00 | 0 | 400 | 0 | 0 | 80 |
| 3 | 12.00 | 0 | 200 | 30 | 0 | 0 |
| | 24.00 | 0 | 400 | 0 | 0 | 0 |
| 4 | 24.00 | 0 | 400 | 0 | 0 | 0 |
| 5 | 12.00 | 0 | 200 | 0 | 0 | 0 |
| | 24.00 | 0 | 400 | 0 | 0 | 0 |
| 6 | 12.00 | 0 | 200 | 0 | 0 | 0 |
| | 24.00 | 0 | 400 | 0 | 0 | 0 |
| 7 | 12.00 | 0 | 200 | 0 | 30 | 100 |
| | 24.00 | 0 | 400 | 0 | 0 | 0 |
| 8 | 12.00 | 0 | 200 | 0 | 0 | 0 |
| | 24.00 | 0 | 400 | 0 | 0 | 0 |
| 9 | 12.00 | 0 | 200 | 0 | 0 | 0 |
| | 24.00 | 0 | 400 | 0 | 0 | 0 |
| 10 | 12.00 | 0 | 200 | 0 | 0 | 0 |
| | 24.00 | 0 | 400 | 0 | 0 | 0 |
| 11 | 12.00 | 0 | 200 | 0 | 30 | 90 |
| | 24.00 | 0 | 400 | 60 | 0 | 0 |
| 12 | 12.00 | 0 | 200 | 0 | 0 | 0 |
| | 24.00 | 0 | 400 | 0 | 0 | 0 |
| 13 | 12.00 | 0 | 200 | 0 | 0 | 0 |
| | 24.00 | 100 | 400 | 0 | 0 | 0 |
| 14 | 12.00 | 0 | 200 | 0 | 0 | 0 |
| | 24.00 | 0 | 400 | 0 | 0 | 0 |
| 15 | 12.00 | 0 | 200 | 0 | 0 | 0 |
| | 24.00 | 0 | 400 | 0 | 0 | 0 |
| 16 | 12.00 | 0 | 200 | 0 | 0 | 0 |
| | 24.00 | 0 | 400 | 0 | 0 | 0 |
| 17 | 12.00 | 0 | 200 | 0 | 0 | 0 |
| | 24.00 | 0 | 400 | 0 | 0 | 0 |
| 18 | 12.00 | 0 | 200 | 0 | 0 | 0 |
| | 24.00 | 0 | 400 | 0 | 0 | 0 |
| 19 | 12.00 | 0 | 200 | 0 | 0 | 0 |
| | 24.00 | 0 | 400 | 0 | 0 | 90 |
| 20 | 12.00 | 0 | 200 | 0 | 0 | 0 |
| | 24.00 | 0 | 400 | 0 | 100 | 0 |
| | 0 | 400 | 0 | 0 | 0 | |
| 21 | 12.00 | 100 | 200 | 0 | 80 | 100 |
| | 24.00 | 100 | 400 | 0 | 60 | 80 |
| 22 | 12.00 | 0 | 200 | 0 | 0 | 0 |
| | 24.00 | 0 | 400 | 0 | 0 | 0 |
| 23 | 12.00 | 100 | 200 | 0 | 0 | 0 |
| | 24.00 | 0 | 400 | 0 | 0 | 0 |
| 24 | 12.00 | 0 | 200 | 0 | 0 | 0 |
| | 24.00 | 0 | 400 | 0 | 0 | 0 |
| 25 | 12.00 | 0 | 200 | 0 | 0 | 0 |
| | 24.00 | 0 | 400 | 0 | 0 | 0 |
| 26 | 12.00 | 0 | 200 | 0 | 0 | 0 |
| | 24.00 | 0 | 400 | 0 | 0 | 0 |
| 27 | 12.00 | 0 | 200 | 0 | 0 | 0 |
| | 24.00 | 0 | 400 | 0 | 0 | 0 |
| 28 | 12.00 | 0 | 200 | 0 | 90 | 30 |
| | 24.00 | 0 | 400 | 0 | 0 | 0 |
| 29 | 12.00 | 0 | 200 | 0 | 0 | 0 |
| | 24.00 | 0 | 400 | 0 | 0 | 0 |
| 30 | 12.00 | 0 | 200 | 0 | 0 | 0 |
| | 24.00 | 0 | 400 | 90 | 0 | 0 |
| 31 | 12.00 | 0 | 200 | 100 | 20 | 90 |
| | 24.00 | 0 | 400 | 80 | 100 | 0 |
| 32 | 12.00 | 0 | 200 | 0 | 0 | 0 |
| | 24.00 | 0 | 400 | 0 | 0 | 0 |
| 33 | 12.00 | 0 | 200 | 0 | 80 | 40 |
| | 24.00 | 0 | 400 | 0 | 0 | 0 |
| 34 | 12.00 | 0 | 200 | 0 | 0 | 0 |
| | 24.00 | 0 | 400 | 0 | 0 | 0 |
| 35 | 12.00 | 0 | 200 | 0 | 0 | 0 |
| | 24.00 | 0 | 400 | 0 | 0 | 30 |
| 36 | 12.00 | 0 | 200 | 0 | 0 | 0 |
| | 24.00 | 0 | 400 | 0 | 0 | 0 |
| 37 | 12.00 | 0 | 200 | 0 | 90 | 0 |
| | 24.00 | 0 | 400 | 0 | 0 | 0 |
| 38 | 12.00 | 0 | 200 | 0 | 0 | 0 |
| | 24.00 | 0 | 400 | 0 | 0 | 0 |
| 39 | 12.00 | 0 | 200 | 0 | 0 | 0 |
| | 24.00 | 0 | 400 | 0 | 0 | 10 |

-continued

MITE & INSECT SCREEN

| EXAMPLE NUMBER | CRW RATE PPM | CRW RESULTS % | SAW SM & MA RATE PPM | SAW RESULTS % | SM RESULTS % | MA RESULTS % |
|---|---|---|---|---|---|---|
| 40 | 12.00 | 0 | 200 | 0 | 0 | 0 |
|    | 24.00 | 0 | 400 | 0 | 20 | 80 |
| 41 | 12.00 | 0 | 200 | 0 | 0 | 0 |
|    | 24.00 | 60 | 400 | 0 | 100 | 100 |
| 42 | 12.00 | 0 | 200 | 0 | 0 | 100 |
|    | 24.00 | 0 | 400 | 0 | 100 | 100 |
| 43 | 12.00 | 0 | 200 | 0 | 90 | 90 |
|    | 24.00 | 0 | 400 | 0 | 80 | 80 |
| 44 | 24.00 | 0 | 400 | 0 | 0 | 0 |
| 45 | 12.00 | 0 | 200 | 0 | 90 | 90 |
|    | 24.00 | 0 | 400 | 0 | 100 | 90 |
| 46 | 12.00 | 0 | 200 | 0 | 80 | 90 |
|    | 24.00 | 0 | 400 | 0 | 80 | 60 |
| 47 | 12.00 | 100 | 200 | 100 | 90 | 100 |
|    | 24.00 | 80 | 400 | 0 | 100 | 100 |
| 48 | 12.00 | 60 | 200 | 0 | 0 | 0 |
|    | 24.00 | 100 | 400 | 0 | 0 | 80 |
| 49 | 12.00 | 0 | 200 | 80 | 0 | 0 |
|    | 24.00 | 0 | 400 | 0 | 0 | 0 |
| 50 | 12.00 | 0 | 200 | 0 | 0 | 0 |
|    | 24.00 | 0 | 400 | 0 | 100 | 100 |
| 51 | 12.00 | 0 | 200 | 0 | 100 | 90 |
|    | 24.00 | 0 | 400 | 0 | 80 | 80 |
| 52 | 12.00 | 0 | 200 | 0 | 0 | 80 |
|    | 24.00 | 0 | 400 | 0 | 0 | 100 |
| 53 | 12.00 | 0 | 200 | 0 | 0 | 0 |
|    | 24.00 | 0 | 400 | 0 | 30 | 60 |
| 54 | 12.00 | 0 | 200 | 0 | 100 | 100 |
|    | 24.00 | 0 | 400 | 40 | 60 | 40 |
| 55 | 12.00 | 0 | 200 | 0 | 0 | 0 |
|    | 24.00 | 0 | 400 | 0 | 0 | 0 |
| 56 | 12.00 | 0 | 200 | 0 | 0 | 0 |
|    | 24.00 | 0 | 400 | 0 | 0 | 0 |
| 57 | 12.00 | 0 | 200 | 0 | 0 | 0 |
|    |       | 0 | 200 | 0 | 0 | 0 |
|    | 24.00 | 0 | 400 | 0 | 0 | 0 |
|    |       | 0 | 400 | 0 | 0 | 0 |
| 58 | 12.00 | 0 | 200 | 0 | 0 | 0 |
|    | 24.00 | 0 | 400 | 0 | 0 | 0 |
| 59 | 12.00 | 0 | 200 | 0 | 0 | 0 |
|    | 24.00 | 0 | 400 | 0 | 0 | 0 |
| 60 | 12.00 | 0 | 200 | 0 | 0 | 50 |
|    | 24.00 | 0 | 400 | 0 | 80 | 60 |
| 61 | 12.00 | 0 | 200 | 0 | 90 | 90 |
|    | 24.00 | 0 | 400 | 0 | 0 | 0 |
| 62 | 12.00 | 0 | 200 | 0 | 0 | 0 |
|    | 24.00 | 0 | 400 | 0 | 0 | 0 |
| 63 | 12.00 | 0 | 200 | 0 | 0 | 0 |
|    | 24.00 | 0 | 400 | 0 | 50 | 80 |
| 64 | 12.00 | 0 | 200 | 0 | 0 | 0 |
|    | 24.00 | 0 | 400 | 0 | 0 | 0 |
| 65 | 12.00 | 0 | 200 | 0 | 0 | 0 |
|    | 24.00 | 0 | 400 | 0 | 0 | 0 |
| 66 | 12.00 | 0 | 200 | 0 | 0 | 0 |
|    | 24.00 | 0 | 400 | 0 | 0 | 0 |
| 67 | 12.00 | 0 | 200 | 0 | 100 | 100 |
|    | 24.00 | 0 | 400 | 0 | 100 | 100 |
| 68 | 24.00 | 0 | 400 | 100 | 30 | 90 |
| 69 | 24.00 | 0 | 400 | 0 | 90 | 90 |
| 70 | 24.00 | 0 | 400 | 0 | 0 | 0 |
| 71 | 24.00 | 0 | 400 | 0 | 0 | 0 |
| 72 | 24.00 | 0 | 400 | 60 | 0 | 100 |
| 73 | 12.00 | 0 | 200 | 0 | 0 | 0 |
|    | 24.00 | 0 | 400 | 100 | 0 | 90 |
| 74 | 24.00 | 0 | 400 | 0 | 100 | 90 |
| 75 | 24.00 | 0 | 400 | 40 | 0 | 0 |
| 76 | 24.00 | 60 | 400 | 0 | 0 | 0 |
| 77 | 12.00 | 0 | 200 | 0 | 50 | 100 |
|    | 24.00 | 0 | 400 | 0 | 90 | 80 |
| 78 | 12.00 | 0 | 200 | 0 | 20 | 90 |
|    | 24.00 | 0 | 400 | 100 | 0 | 100 |
| 79 | 24.00 | 0 | 400 | 0 | 0 | 0 |
| 80 | 12.00 | 0 | 200 | 0 | 0 | 0 |
|    | 24.00 | 0 | 400 | 0 | 0 | 0 |
| 81 | 24.00 | 0 | 400 | 0 | 0 | 0 |

-continued

| EXAMPLE NUMBER | CRW RATE PPM | CRW RESULTS % | SAW SM & MA RATE PPM | SAW RESULTS % | SM RESULTS % | MA RESULTS % |
|---|---|---|---|---|---|---|
| | 24.00 | 0 | 400 | 0 | 0 | 0 |

COMPOSITIONS

The compounds of this invention are applied in the form of compositions which are important embodiments of the invention, and which comprise a compound of this invention and a phytologically-acceptable inert carrier. The compositions are either concentrated formulations which are dispersed in water for application, or are dust or granular formulations which are applied without further treatment. The compositions are prepared according to procedures and formulae which are conventional in the agricultural chemical art, but which are novel and important because of the presence therein of the compounds of this invention. Some description of the formulation of the compositions will be given, however, to assure that agricultural chemists can readily prepare any desired composition.

The dispersions in which the compounds are applied are most often aqueous suspensions or emulsions prepared from concentrated formulations of the compounds. Such water-soluble, water-suspendable or emulsifiable formulations are either solids usually known as wettable powders, or liquids usually known as emulsifiable concentrates or aqueous suspensions. Wettable powders, which may be compacted to form water dispersible granules, comprise an intimate mixture of the active compound, an inert carrier and surfactants. The concentration of the active compound is usually from about 10% to about 90% by weight. The inert carrier is usually chosen from among the attapulgite clays, the montmorillonite clays, the diatomaceous earths, or the purified silicates. Effective surfactants, comprising from about 0.5% to about 10% of the wettable powder, are found among the sulfonated lignins, the condensed naphthalenesulfonates, the naphthalenesulfonates, the alkylbenzenesulfonates, the alkyl sulfates, and nonionic surfactants such as ethylene oxide adducts of alkyl phenols.

Emulsifiable concentrates of the compounds comprise a convenient concentration of a compound, such as from about 50 to about 500 grams per liter of liquid, equivalent to about 10% to about 50%, dissolved in an inert carrier which is either a water miscible solvent or a mixture of water-immiscible organic solvent and emulsifiers. Useful organic solvents include aromatics, especially the xylenes, and the petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional non-ionic surfactants, such as those discussed above.

Aqueous suspensions comprise suspensions of water-insoluble compounds of this invention, dispersed in an aqueous vehicle at a concentration in the range from about 5% to about 50% by weight. Suspensions are prepared by finely grinding the compound, and vigorously mixing it into a vehicle comprised of water and surfactants chosen from the same types discussed above. Inert ingredients, such as inorganic salts and synthetic or natural gums, may also be added, to increase the density and viscosity of the aqueous vehicle. It is often most effective to grind and mix the compound at the same time by preparing the aqueous mixture, and homogenizing it in an implement such as a sand mill, ball mill, or piston-type homogenizer.

The compounds may also be applied as granular compositions, which are particularly useful for applications to the soil. Granular compositions usually contain from about 0.5% to about 10% by weight of the compound, dispersed in an inert carrier which consists entirely or in large part of clay or a similar inexpensive substance. Such compositions are usually prepared by dissolving the compound in a suitable solvent, and applying it to a granular carrier which has been pre-formed to the appropriate particle size, in the range of from about 0.5 to 3 mm. Such compositions may also be formulated by making a dough or paste of the carrier and compound, and crushing and drying to obtain the desired granular particle size.

Dusts containing the compounds are prepared simply by intimately mixing the compound in powdered form with a suitable dusty agricultural carrier, such as kaolin clay, ground volcanic rock and the like. Dusts can suitably contain from about 1% to about 10% of the compound.

It is equally practical, when desirable for any reason, to apply the compound in the form of a solution in an appropriate organic solvent, usually a bland petroleum oil, such as the spray oils, which are widely used in agricultural chemistry.

Insecticides and miticides are generally applied in the form of a dispersion of the active ingredient in a liquid carrier. It is conventional to refer to application rates in terms of the concentration of active ingredient in the carrier. The most widely used carrier is water.

The compounds of the invention can also be applied in the form of an aerosol composition. In such compositions the active compound is dissolved or dispersed in an inert carrier, which is a pressure-generating propellant mixture. The aerosol composition is packaged in a container from which the mixture is dispensed through an atomizing valve. Propellant mixtures comprise either low-boiling halocarbons, which may be mixed with organic solvents, or aqueous suspensions pressurized with inert gases or gaseous hydrocarbons.

The actual amount of compound to be applied to loci of insects and mites is not critical and can readily be determined by those skilled in the art in view of the examples above. In general, concentrations of from 10 ppm to 5000 ppm of compound are expected to provide good control. With many of the compounds, concentrations of from 100 to 1500 ppm will suffice. For field crops, such as soybeans and cotton, a suitable application rate for the compounds is about 0.5 to 1.5 lb/A, typically applied in 50 gal/A of spray formulation containing 1200 to 3600 ppm of compound. For citrus crops, a suitable application rate is from about 100 to 1500 gal/A spray formulation, which is a rate of 100 to 1000 ppm.

The locus to which a compound is applied can be any locus inhabited by an insect or arachnid, for example, vegetable crops, fruit and nut trees, grape vines, and ornamental plants. Inasmuch as many mite species are specific to a particular host, the foregoing list of mite species to provides exemplification of the wide range of settings in which the present compounds can be used.

Because of the unique ability of mite eggs to resist toxicant action, repeated applications may be desirable to control newly emerged larvae, as is true of other known acaricides.

The following formulations of compounds of the invention are typical of compositions useful in the pracitice of the present invention.

| A. 0.75 Emulsifiable Concentrate | |
|---|---|
| 5-methyl-N-[2-(4-methoxyphenyl)ethyl]-5,6-dimethylfuro[2,3-d]pyrimidin-4-amine | 9.38% |
| "TOXIMUL D" (nonionic/anionic surfactant blend) | 2.50% |
| "TOXIMUL H" (nonionic/anionic surfactant blend) | 2.50% |
| "EXXON 200" (naphthalenic solvent) | 85.62% |
| B. 1.5 Emulsifiable Concentrate | |
| 5-methyl-N-[2-(2-naphthyl)ethyl]furo-[2,3-d]pyrimidin-4-amine | 18.50% |
| "TOXIMUL D" | 2.50% |
| "TOXIMUL H" | 2.50% |
| "EXXON 200" | 76.50% |
| C. 0.75 Emulsifiable Concentrate | |
| N-[2-[4-(1,1,2,2-tetrafluoroethoxy)-phenyl]ethyl]-5,6-dimethylfuro[2,3-d]-pyrimidin-4-amine | 9.38% |
| "TOXIMUL D" | 2.50% |
| "TOXIMUL H" | 2.50% |
| "EXXON 200" | 85.62% |
| D. 1.0 Emulsifiable Concentrate | |
| 5,6-dimethyl-4-[2-[4-[4-(trifluoro-methyl)phenoxy]phenyl]ethoxy]furo[2,3-d]-pyrimidine | 12.50% |
| N-methylpyrrolidone | 25.00% |
| "TOXIMUL D" | 2.50% |
| "TOXIMUL H" | 2.50% |
| "EXXON 200" | 57.50% |
| E. 1.0 Aqueous Suspension | |
| 5,6-dimethyl-4-[2-[4-(n-butoxy)phenyl]-ethoxy]furo[2,3-d]pyrimidine | 12.00% |
| "PLURONIC P-103" (block copolymer of propylene oxide and ethylene oxide, surfactant) | 1.50% |
| "PROXEL GXL" (biocide/preservative) | .05% |
| "AF-100" (silicon based antifoam agent) | .20% |
| "REAX 88B" (lignosulfonate dispersing agent) | 1.00% |
| propylene glycol | 10.00% |
| veegum | .75% |
| xanthan | .25% |
| water | 74.25% |
| F. 1.0 Aqueous Suspension | |
| 5-methyl-N-[2-(4-methoxyphenyl)ethyl]-furo[2,3-d]pyrimidin-4-amine | 12.50% |
| "MAKON 10" (10 moles ethyleneoxide nonylphenol surfactant) | 1.00% |
| "ZEOSYL 200" (silica) | 1.00% |
| "AF-100" | 0.20% |
| "AGRIWET FR" (surfactant) | 3.00% |
| 2% xanthan hydrate | 10.00% |
| water | 72.30% |
| G. 1.0 Aqueous Suspension | |
| 5-methyl-N-[2-(4-chlorophenyl)ethyl]-furo[2,3-d]pyrimidin-4-amine | 12.50% |
| "MAKON 10" | 1.50% |
| "ZEOSYL 200" (silica) | 1.00% |
| "AF-100" | 0.20% |
| "POLYFON H" (lignosulfonate dispersing agent) | 0.20% |
| 2% xanthan hydrate | 10.00% |
| water | 74.60% |
| H. Wettable Powder | |
| 5,6-dimethyl-4-[2-[4-[4-(trifluoro-methyl)phenoxy]phenyl]ethoxy]furo[2,3-d]-pyrimidine | 25.80% |
| "POLYFON H" | 3.50% |
| "SELLOGEN HR" | 5.00% |
| "STEPANOL ME DRY" | 1.00% |
| gum arabic | 0.50% |
| "HISIL 233" | 2.50% |
| Barden clay | 61.70% |
| I. 1.0 Aqueous Suspension | |
| 5,6-dimethyl-4-[2-[4-[4-(trifluoro-methyl)phenoxy]phenyl]ethoxy]furo[2,3-d]-pyrimidine | 12.40% |
| "TERGITOL 158-7" | 5.00% |
| "ZEOSYL 200" | 1.00% |
| "AF-100" | 0.20% |
| "POLYFON H" | 0.50% |
| 2% xanthan solution | 10.00% |
| tap water | 70.90% |
| J. 1.0 Emulsifiable Concentrate | |
| 5-methyl-N-[2-(2-naphthyl)ethyl]-furo[2,3-d]pyrimidin-4-amine | 12.40% |
| "TOXIMUL D" | 2.50% |
| "TOXIMUL H" | 2.50% |
| "EXXON 200" | 82.60% |
| K. Wettable Powder | |
| 5,6-dimethyl-4-[2-[4-(n-butoxy)phenyl]-ethoxy]furo[2,3-d]pyrimidine | 25.80% |
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |
| L. 0.5 Emulsifiable Concentrate | |
| 5-methyl-N-[2-(2-naphthyl)ethyl]furo-[2,3-d]pyrimidin-4-amine | 6.19% |
| "TOXIMUL H" | 3.60% |
| "TOXIMUL D" | 0.40% |
| "EXXON 200" | 89.81% |
| M. Wettable Powder | |
| 5-methyl-N-[2-(4-methoxyphenyl)ethyl]-furo[2,3-d]pyrimidin-4-amine | 25.80% |
| "SELLOGEN HR" | 5.00% |
| "POLYFON H" | 4.00% |
| "STEPANOL ME DRY" | 2.00% |
| "HISIL 233" | 3.00% |
| Barden clay | 60.20% |
| N. 1.0 Aqueous Suspension | |
| N-[2-[4-(1,1,2,2-tetrafluoroethoxy)-phenyl]ethyl]-5,6-dimethylfuro[2,3-d]-pyrimidin-4-amine | 12.40% |
| "TERGITOL 158-7" | 5.00% |
| "EEOSYL 200" | 1.00% |
| "POLYFON H" | 0.50% |
| "AF-100" | 0.20% |
| xanthan solution (2%) | 10.00% |
| tap water | 70.90% |

We claim:

1. A compound of the formula (7)

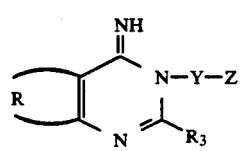

(7)

where

R is

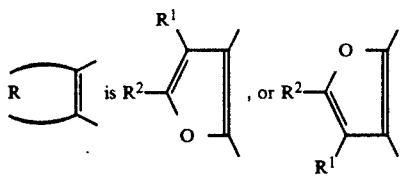

R¹ is H, C₁-C₄ alkyl, or phenyl optionally substituted with halo, (C₁-C₄), alkoxy;

R² is H, (C1-C4) alkyl, nitro, halo; or

R¹ and R² combine to form —(CH₂)₄—;

R³ is H, (C₁₋C₄) alkyl, halo (C₁-CH₄ alkyl, phenyl, or substituted phenyl;

Y is a bivalent hydrocarbon radical two to six carbon atoms long, optionally substitued with (C₁-C₄) alkyl, (C₂-C₄) alkenyl or alkynyl, branched (C₃-C₇) alkyl, (C₃ₗ-C₇) cycloalkyl or cycloalkenyl, halo, halo (C₁-C₄) alkyl, halo (C₁-C₄) alkoxy, hydroxy, or (C₁-C₄) acyl; and Z is (a) (C₃-C₈) cycloalkyl or cycloalkenyl, optionally substituted with (C₁-C₄) alkyl, (C₁-C₄) alkoxy, halo (C₁-C₄) alkyl, halo (C₁-C₄) alkoxy, halo, hydroxy or (C₁-C₄) acyl;

(b) a phenyl group of the formula (2)

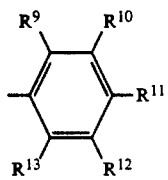

(2)

where
R⁹ to R¹³ are independently
H,
halo
I,
(C₃-C₈) cycloalkyl or -cycloalkenyl,
phenoxy, or
substituted phenoxy,
phenylthio, or substituted phenylthio,
phenyl, or substituted phenyl,
NO₂,
acetoxy,
OH,
CN,
SiR⁷R¹⁴ or OSiR⁷R⁸R¹⁴, where R⁷, and R⁸ are as defined above and R¹⁴ is (C₁-C₄) alkyl, (C₃-C₄) branched alkyl, phenyl, or substituted phenyl.
NR¹⁵R¹⁶, where R¹⁵ and R¹⁶ are independently H, (C₁-C₄) alkyl, or (C₁-C₄) acyl,
S(O)R¹⁷, or SO₂R¹⁷, where R¹⁷ is (C₁-C₄) alkyl phenyl, or substituted phenyl;
a C₁-C₄ saturted on unsaturated hydrocarbon chain, straight chain or branched optionally including a hetero atom selected from O, S, SO, SO₂, NR⁴, or SiR⁷R⁸, where R⁴, R⁷ and R⁸ are as defined above, and optionally substituted with halo, halo (C₁-C₄) alkoxy, hydroxy, (C₃-C₈) cycloalkyl or cycloalkeny, (C₁-C₄) aryl, phenoxy, substituted phenoxy, phenyl, substituted phenyl, phenylthio, or substituted phenylthio;
(C₁-C₇) alkoxy optionally substituted with halo, phenyl, substituted phenyl, (C₃ₗ-C₈) cycloalkyl or cycloalkenyl, phenoxy, or substituted phenoxy,
(C₁-C₇) alkylthio optionally substituted with halo, phenyl, substituted phenyl (C₃-C₈) cycloalkyl or cycloalkenyl, phenoxy, or substituted phenoxyl; or
R¹⁰ and R¹¹ combine to form —O—CF₂—O—;

(c) a furyl group of formula (3)

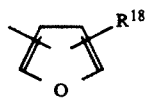

(3)

where R¹⁸ is H, halo, halomethyl, CN, NO₂, (C₁-C₄) alkyl, (C₃-C₄) branched alkyl, phenyl, (C₁-C₄) alkoxy;

(d) a thienyl group of the formula (4)

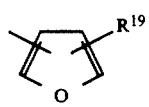

(4)

where R¹⁹ and R¹⁸ are defined in paragraph (d) or thientyl;

(e) a group selected from
optionally substituted naphthyl, dihydronaphthyl, tetrahydronaphthyl, and decahydro-naphthyl; and
optionally substituted pyridyl;

where, in the foregoing definitions, the term substituted phenyl refers to phenyl substituted with up to three groups selected from halo, I, (C₁-C₁₀) alkyl, branched (C₃-C₆) alkyl, halo (C₁-C) alkoxy, phenoxy, substituted phenoxy, phenyl, substituted phenyl, NO₂, OH, CN (C₁-C₄) alkanoyloxy or benzyloxy;

the term substituted phenoxy refers to a phenoxy group substituted with up to three groups selected from halo, I, (C₁-C₁₀) alkyl, branched (C₃-C₆) alkyl, halo (C₁-C₇) alkyl, hydroxy (C₁-C₇) alkyl, (C₁-C₇) alkoyx, halo (C₁-C₇) alkoxy, phenoxy, substituted phenoxy phenyl, substituted phenyl, NO₂, OH, CN, (C₁-C₄) alkanoyloxy, or benzyloxy;

the term substituted phenylthio refers to a phenylthio group substituted with up to three groups selected from halo, I, (C₁-C₁₀) alkyl, branched (C₃-C₆) alkyl, halo (C₁-C₇) alkoxy, hydroxy (C₁-C₇) alkyl, C₁-C₇) alkoxy, halo (C₁-C₇) alkoxy, phenoxy, substituted phenoxy, phenyl, substituted phenyl, NO₂, OH, CN, (C₁-C₄) alkanoyloxy, or benzyloxy; and the term substituted phenylsulfonyl refers to a phenylsulfonyl group substituted with up to three groups selected from halo, I, (C₁-C₁₀) alkyl, branched (C₃-C₆) alkyl, halo (C₁-C₇) alkyl, hydroxy (C₁-C₇) alkyl, (C₁-C₇) alkoxy, halo (C₁-C₇) alkoxy, phenoxy, substituted phenoxy, phenyl, substituted phenyl, NO₂, OH, CN, (C₁-C₄) alkanoyloxy, or benzyloxy.

2. A compound of claim 1 wherein Y is —CH₂CH₂—.

3. A compound of claim 1 wherein

4. A compound of claim 1 wherein

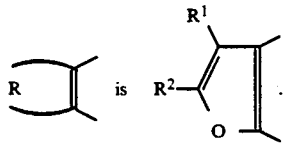

5. A compound of claim 1 wherein

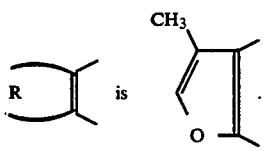

6. A compound of claim 1 wherein

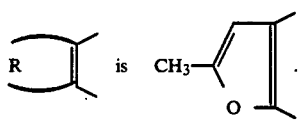

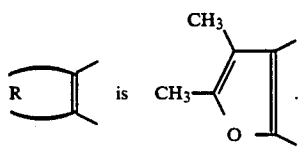

7. A compound of claim 1 wherein Z is a phenyl group or substituted phenyl group.

8. A compound of claim 7 wherein Z is a substituted phenyl group of formula (2) wherein one of the substituents R9 to R13 is a haloalkoxy group.

9. A compound of claim 8 wherein Z is 4-(1,1,2,2-tetrafluoroethoxy)phenyl.

10. A compound of claim 7 wherein Z is a substituted phenyl group of formula (2) wherein one of the substituents $R^9$ to $R^{13}$ is a haloalkyl group.

11. A compound of claim 10 wherein Z is 3-(halo(C$_1$–C$_4$)alkylphenyl.

12. A compound of claim 10 wherein Z is 4-(halo(C$_1$–C$_4$)alkylphenyl.

13. A compound of claim 10 wherein Z is phenyl substituted with trifluoromethyl.

14. A compound of claim 7 wherein Z is a phenyl group of formula (2) wherein one of the substituents $R^9$ to $R^{13}$ is a branched (C$_3$–C$_7$)alkyl group.

15. A compound of claim 14 wherein Z is 4-(t-butyl)-phenyl.

16. A compound of claim 1 which is 3-[2-(4-methoxyphenyl)ethyl]-5,6-dimethylfuro[2,3,-d]pyrimidin-4(3H)-imine.

17. A compound of claim 1 which is 3-[2-(2-naphthyl)ethyl]-5,6-dimethylfuro[2,3,-d]pyrimidin-4(3H)-imine.

18. A compound of claim 8 which is 3-[2-(3-trifluoromethyl)phenyl)ethyl]-5,6-dimethylfuro[2,3,-d]pyrimidin-4(3H)-imine.

19. A fungicide composition which comprises a compound of claim 1 in combination with a phytologically-acceptable carrier.

20. A fungicidal method which comprises applying to the locus of a plant pathogen a phytologically-acceptable amount of a compound of claim 1.

* * * * *